(12) United States Patent
Kim

(10) Patent No.: US 10,118,971 B2
(45) Date of Patent: Nov. 6, 2018

(54) PROTEIN IN WHICH ELECTRICAL INTERACTION IS INTRODUCED WITHIN HYDROPHOBIC INTERACTION SITE AND PREPARATION METHOD THEREFOR

(71) Applicant: IBENTRUS, INC., Daejeon (KR)

(72) Inventor: Hoeon Kim, Gyeonggi-do (KR)

(73) Assignee: IBENTRUS, INC., Daejeon (KR)

( * ) Notice: Subject to any disclaimer, the term of this patent is extended or adjusted under 35 U.S.C. 154(b) by 32 days.

(21) Appl. No.: 14/776,045

(22) PCT Filed: Mar. 13, 2014

(86) PCT No.: PCT/KR2014/002139
§ 371 (c)(1),
(2) Date: Dec. 29, 2015

(87) PCT Pub. No.: WO2014/142591
PCT Pub. Date: Sep. 18, 2014

(65) Prior Publication Data
US 2016/0152726 A1    Jun. 2, 2016

Related U.S. Application Data

(60) Provisional application No. 61/780,390, filed on Mar. 13, 2013.

(51) Int. Cl.
| | |
|---|---|
| *C07K 16/00* | (2006.01) |
| *C07K 16/26* | (2006.01) |
| *C07K 16/32* | (2006.01) |
| *C07K 16/24* | (2006.01) |
| *C07K 16/28* | (2006.01) |
| *C07K 16/10* | (2006.01) |
| *C07K 16/46* | (2006.01) |

(52) U.S. Cl.
CPC .............. *C07K 16/32* (2013.01); *C07K 16/00* (2013.01); *C07K 16/1018* (2013.01); *C07K 16/241* (2013.01); *C07K 16/244* (2013.01); *C07K 16/247* (2013.01); *C07K 16/26* (2013.01); *C07K 16/2863* (2013.01); *C07K 16/2866* (2013.01); *C07K 16/2875* (2013.01); *C07K 16/2878* (2013.01); *C07K 16/468* (2013.01); *C07K 2317/21* (2013.01); *C07K 2317/24* (2013.01); *C07K 2317/31* (2013.01); *C07K 2317/515* (2013.01); *C07K 2317/522* (2013.01); *C07K 2317/526* (2013.01); *C07K 2319/00* (2013.01); *C07K 2319/30* (2013.01); *C07K 2319/32* (2013.01)

(58) Field of Classification Search
CPC ........ C07K 16/00; C07K 16/26; C07K 16/32; C07K 16/241; C07K 16/244; C07K 16/468; C07K 16/2866; C07K 16/2875; C07K 16/2878; C07K 2317/31; C07K 2317/21; C07K 2317/24; C07K 2317/56; C07K 2317/515; C07K 2317/522; C07K 2317/526; C07K 2319/00; C07K 2319/30; C07K 2319/32

See application file for complete search history.

(56) References Cited

U.S. PATENT DOCUMENTS

2005/0079184 A1* 4/2005 Hsing-Chang ..... C07K 16/2803
424/178.1

FOREIGN PATENT DOCUMENTS

| | | |
|---|---|---|
| CN | 101627053 | 1/2010 |
| KR | 10-2008-0013875 A | 2/2008 |
| WO | 2009/089004 | 7/2009 |
| WO | 2011-143545 A | 11/2011 |
| WO | 2012-123949 A | 9/2012 |
| WO | 2013/065708 | 5/2013 |

OTHER PUBLICATIONS

International Search Report for PCT/KR2014/002139, dated May 6, 2014.*
Maria Aiko Angela A. Diaz : "Effects of engineering charged amono acids in the CH3 domains on antibody heavy chain dimerization" Philippine Science Letters, vol. 4, No. 1, May 27, 2011, p. 48-55.
K. Gunasekaran et al: "Enhancing Antibody Fc Heterodimer Formation through Electrostatic Steering Effects: ~" Journal of Biological Chemistry, vol. 285, No. 25, Jun. 18, 2010, p. 19637-19646.
EPO, Partial Supplementary European Search Report of Application No. 14764140.1, dated Oct. 26, 2016.
EPO, Extended European Search Report of Application No. 14764140.1, dated Feb. 1, 2017.

* cited by examiner

*Primary Examiner* — Robert S Landsman
*Assistant Examiner* — Bruce D. Hissong
(74) *Attorney, Agent, or Firm* — Lex IP Meister, PLLC

(57) ABSTRACT

The present invention provides a protein or antibody in which, of a pair of hydrophobic amino acids selected from within a hydrophobic interaction site of the protein, one hydrophobic amino acid is transformed into a substance having a positive electrical charge and the other hydrophobic amino acid is transformed into a substance having a negative electrical charge, and electrostatic interaction is introduced within the hydrophobic interaction site of the protein by means of the positive charge and the negative charge. The present invention also provides a method for preparing the protein or antibody, and a method for measuring the degree of coupling between a heavy chain and a light chain, using the antibody. The protein or antibody in accordance with to the present invention has a low contamination by a homodimer or a monomer, and thus a heterodimer can be obtained in high purity.

9 Claims, 20 Drawing Sheets

Specification includes a Sequence Listing.

10 Natural Variants by Combinatorial Association

FIG. 4

```
             .231        .241        .251        .261        .271        .281        .291        .301        .311        .321
Human IgG1   APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPA
Human IgG2   APP-VAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPA
Human IgG3   APELLGGPSVFLFPPKPKDTLMISRTPEVTCVVVDVSHEDPEVQFKWYVDGVEVHNAKTKPREEQYNSTFRVVSVLTVLHQDWLNGKEYKCKVSNKALPA
Human IgG4   APEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPS
Mouse IgG1   VPEV---SSVFIFPPKPKDVLTITLTPKVTCVVVDISKDDPEVQFSWFVDDVEVHTAQTQPREEQFNSTFRSVSELPIMHQDWLNGKEFKCRVNSAAFPA
Mouse IgG2aa APNLLGGPSVFIFPPNIKDVLMISLSPIVTCVVVDVSEDDPDVQISWFVNNVEVHTAQTQTHREDYNSTLRVVSALPIQHQDWMSGKEFKCKVNNKDLPA
Mouse IgG2ab APDLLGGPSVFIFPPKIKDVLMISLSPMVTCVVVDVSEDDPDVQISWFVNNVEVHTAQTQTHREDYNSTLRVVSALPIQHQDWMSGKEFKCKVNNRALPS
Mouse IgG2b  APNLEGGPSVFIFPPNIKDVLMISLLTPKVTCVVVDVSEDPDVQISWFVNNVEVHTAQTQTHREDYNSTIRVVSTLFIQHQDWMSGKEFKCKVNNKDLPS
Mouse IgG3   AGNILGGPSVFIFPPKPKDALMISLLTPKVTCVVVDVSEDDPDVHVSWFVDNKEVHTAWTQPREAQYNSTFRVVSALPIQHQDWMRGKEFKCKVNNKALPA .331        .341        .351        .361        .371        .381        .391        .401        .411        .421
Human IgG1   PIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHE
Human IgG2   PIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHE
Human IgG3   PIEKTISKTKGQPREPQVYTLPPSREEMTKNQVSLTCLVKGFYPSDIAVEWESSGQPENNYNTTPPMLDSDGSFFLYSKLTVDKSRWQQGNIFSCSVMHE
Human IgG4   SIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHE
Mouse IgG1   PIEKTISKTKGRPKAPQVYTIPPPKEQMAKDKVSLTCMITDFFPEDITVEWQWNGQPAENYKNTQPIMNTNGSYFVYSKLNVQKSNWEAGNTFTCSVLHE
Mouse IgG2aa PIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHE
Mouse IgG2ab PIEKTISKPRGPVGPVRAPQVYVLPPPAEEMTKKEFSLTCMITGFLPAEIAVDWTSNGRTEQNYKNTATVLDSDGSYFMYSKLRVQKSTWERGSLFACSVVHE
Mouse IgG2b  PIERTISKIKGLVRAPQVYTLPPAEQLSRKDVSLTCLVRGFYPKDIAVEWTSNGHTEENYKDTAPVLDSDGSYFIYSKLNMKTSKWEKTDSFSCNVRHE
Mouse IgG3   PIERTISKPKGRAQTPQVYTIPPPREQMSKKKKVSLTCLVTNFFSEAISVEWERNGELEQDYKNTPPILDSDGTYFLYSKLTVDTDSWLQGEIFTCSVHE .431        .441
Human IgG1   ALHNHYTQKSLSLSPGK (SEQ ID NO: 1)
Human IgG2   ALHNHYTQKSLSLSPGK (SEQ ID NO: 2)
Human IgG3   ALHNRFTQKSLSLSPGK (SEQ ID NO: 3)
Human IgG4   ALHNHYTQKSLSLSLGK (SEQ ID NO: 4)
Mouse IgG1   GLHNHTEKSLSHSPGK  (SEQ ID NO: 5)
Mouse IgG2aa GLHNHHTTKSFSRTPGK (SEQ ID NO: 6)
Mouse IgG2ab VLHNHLTTKTISRSLGK (SEQ ID NO: 7)
Mouse IgG2b  GLKNYYLKKTISRSPGK (SEQ ID NO: 8)
Mouse IgG3   ALHNHHTQKNLSRSPGK (SEQ ID NO: 9)
```

| ID | Chain A (CH3) | ID | Chain B (CH3) |
|----|---|----|---|
| A0 | - | B0 | - |
| A1 | L351K | B1 | L351D |
| A2 | P395K | B2 | P395D |
| A3 | Y407K | B3 | Y407D |
| A4 | L351K/P395K | B4 | L351D/P395D |
| A5 | L351K/Y407K | B5 | L351D/Y407D |
| A6 | T394K/P395K | B6 | T394D/P395D |
| A7 | T394K/V397K | B7 | T394D/V397D |
| A8 | P395K/V397K | B8 | P395D/V397D |
| A9 | P395K/Y407K | B9 | P395D/Y407D |
| A10 | L351K/T394K/P395K | B10 | L351D/T394D/P395D |
| A11 | L351K/T394K/V397K | B11 | L351D/T394D/V397D |
| A12 | L351K/P395K/V397K | B12 | L351D/P395D/V397D |
| A13 | L351K/P395K/Y407K | B13 | L351D/P395D/Y407D |
| A14 | L351K/T394K/P395K/V397K | B14 | L351D/T394D/P395D/V397D |

FIG. 9
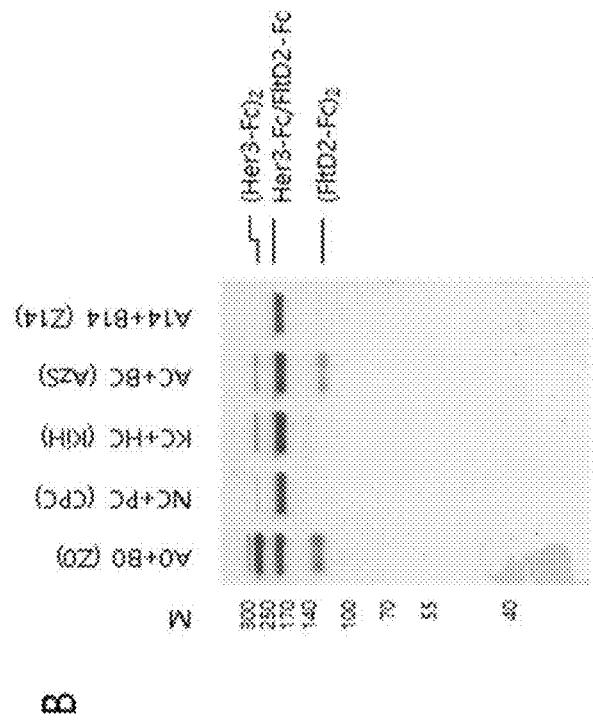
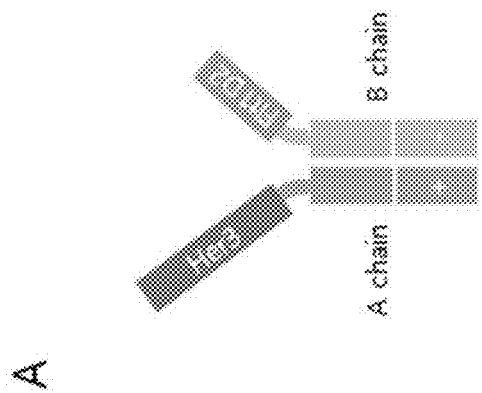

SEQUENCE LISTING

<160> NUMBER OF SEQ ID NOS: 9

<210> SEQ ID NO 1
<211> LENGTH: 217
<212> TYPE: PRT
<213> ORGANISM: Artificial Sequence

```
<220> FEATURE:
<223> OTHER INFORMATION: Synthetic (Fc of Human IgG1, wherein 231st
      residue of full Human IgG1 is designated as 1st residue)

<400> SEQUENCE: 1

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
        210                 215

<210> SEQ ID NO 2
<211> LENGTH: 217
<212> TYPE: PRT
<213> ORGANISM: Artificial Sequence
<220> FEATURE:
<223> OTHER INFORMATION: Synthetic (Fc of Human IgG2, wherein 231st
      residue of full Human IgG2 is designated as 1st residue)
<220> FEATURE:
<221> NAME/KEY: MOD_RES
<222> LOCATION: (4)
<223> OTHER INFORMATION: Xaa is absent

<400> SEQUENCE: 2

Ala Pro Pro Xaa Val Ala Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Gln Phe Asn Trp Tyr
         35                  40                  45

Val Asp Gly Val Glu Val His Asn Ala Lys Thr Lys Pro Arg Glu Glu
     50                  55                  60

Gln Phe Asn Ser Thr Phe Arg Val Val Ser Val Leu Thr Val Val His
 65                  70                  75                  80

Gln Asp Trp Leu Asn Gly Lys Glu Tyr Lys Cys Lys Val Ser Asn Lys
```

```
                        85                  90                  95
Gly Leu Pro Ala Pro Ile Glu Lys Thr Ile Ser Lys Thr Lys Gly Gln
                100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 3
<211> LENGTH: 217
<212> TYPE: PRT
<213> ORGANISM: Artificial Sequence
<220> FEATURE:
<223> OTHER INFORMATION: Synthetic (Fc of Human IgG3, wherein 231st
      residue of full Human IgG3 is designated as 1st residue)

<400> SEQUENCE: 3

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Gln Phe Lys Trp Tyr
            35                  40                  45

Val Asp Gly Val Glu Val His Asn Ala Lys Thr Lys Pro Arg Glu Glu
        50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
                100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215
```

-continued

```
<210> SEQ ID NO 4
<211> LENGTH: 217
<212> TYPE: PRT
<213> ORGANISM: Artificial Sequence
<220> FEATURE:
<223> OTHER INFORMATION: Synthetic (Fc of Human IgG4, wherein 231st
      residue of full Human IgG4 is designated as 1st residue)

<400> SEQUENCE: 4

Ala Pro Glu Phe Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser Gln Glu Asp Pro Glu Val Gln Phe Asn Trp Tyr
         35                  40                  45

Val Asp Gly Val Glu Val His Asn Ala Lys Thr Lys Pro Arg Glu Glu
     50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 5
<211> LENGTH: 217
<212> TYPE: PRT
<213> ORGANISM: Artificial Sequence
<220> FEATURE:
<223> OTHER INFORMATION: Synthetic (Fc of Mouse IgG1, wherein 231st
      residue of full Mouse IgG1 is designated as 1st residue)
<220> FEATURE:
<221> NAME/KEY: MOD_RES
<222> LOCATION: (5)...(7)
<223> OTHER INFORMATION: Xaa is absent

<400> SEQUENCE: 5

Val Pro Glu Val Xaa Xaa Xaa Ser Ser Val Phe Ile Phe Pro Pro Lys
  1               5                  10                  15

Pro Lys Asp Val Leu Thr Ile Thr Leu Thr Pro Lys Val Thr Cys Val
             20                  25                  30

Val Val Asp Ile Ser Lys Asp Asp Pro Glu Val Gln Phe Ser Trp Phe
         35                  40                  45

Val Asp Asp Val Glu Val His Thr Ala Gln Thr Gln Pro Arg Glu Glu
     50                  55                  60
```

```
Gln Phe Asn Ser Thr Phe Arg Ser Val Ser Glu Leu Pro Ile Met His
 65                  70                  75                  80

Gln Asp Trp Leu Asn Gly Lys Glu Phe Lys Cys Arg Val Asn Ser Ala
                 85                  90                  95

Ala Phe Pro Ala Pro Ile Glu Lys Thr Ile Ser Lys Thr Lys Gly Arg
            100                 105                 110

Pro Lys Ala Pro Gln Val Tyr Thr Ile Pro Pro Lys Glu Gln Met
        115                 120                 125

Ala Lys Asp Lys Val Ser Leu Thr Cys Met Ile Thr Asp Phe Phe Pro
130                 135                 140

Glu Asp Ile Thr Val Glu Trp Gln Trp Asn Gly Gln Pro Ala Glu Asn
145                 150                 155                 160

Tyr Lys Asn Thr Gln Pro Ile Met Asn Thr Asn Gly Ser Tyr Phe Val
                165                 170                 175

Tyr Ser Lys Leu Asn Val Gln Lys Ser Asn Trp Glu Ala Gly Asn Thr
                180                 185                 190

Phe Thr Cys Ser Val Leu His Glu Gly Leu His Asn His Thr Glu
                195                 200                 205

Lys Ser Leu Ser His Ser Pro Gly Lys
210                 215

<210> SEQ ID NO 6
<211> LENGTH: 217
<212> TYPE: PRT
<213> ORGANISM: Artificial Sequence
<220> FEATURE:
<223> OTHER INFORMATION: Synthetic (Fc of Mouse IgG2aa, wherein 231st
      residue of full Mouse IgG2aa is designated as 1st residue)

<400> SEQUENCE: 6

Ala Pro Asn Leu Leu Gly Gly Pro Ser Val Phe Ile Phe Pro Pro Lys
  1               5                  10                  15

Ile Lys Asp Val Leu Met Ile Ser Leu Ser Pro Ile Val Thr Cys Val
                 20                  25                  30

Val Val Asp Val Ser Glu Asp Asp Pro Asp Val Gln Ile Ser Trp Phe
             35                  40                  45

Val Asn Asn Val Glu Val His Thr Ala Gln Thr Gln Thr His Arg Glu
 50                  55                  60

Asp Tyr Asn Ser Thr Leu Arg Val Val Ser Ala Leu Pro Ile Gln His
 65                  70                  75                  80

Gln Asp Trp Met Ser Gly Lys Glu Phe Lys Cys Lys Val Asn Asn Lys
                 85                  90                  95

Asp Leu Pro Ala Pro Ile Glu Arg Thr Ile Ser Lys Pro Lys Gly Ser
            100                 105                 110

Val Arg Ala Pro Gln Val Tyr Val Leu Pro Pro Glu Glu Glu Met
        115                 120                 125

Thr Lys Lys Gln Val Thr Leu Thr Cys Met Val Thr Asp Phe Met Pro
130                 135                 140

Glu Asp Ile Tyr Val Glu Trp Thr Asn Asn Gly Lys Thr Glu Leu Asn
145                 150                 155                 160

Tyr Lys Asn Thr Glu Pro Val Leu Asp Ser Asp Gly Ser Tyr Phe Met
                165                 170                 175

Tyr Ser Lys Leu Arg Val Glu Lys Lys Asn Trp Val Glu Arg Asn Ser
                180                 185                 190

Tyr Ser Cys Ser Val Val His Glu Gly Leu His Asn His His Thr Thr
```

```
                    195                 200                 205

Lys Ser Phe Ser Arg Thr Pro Gly Lys
    210                 215

<210> SEQ ID NO 7
<211> LENGTH: 217
<212> TYPE: PRT
<213> ORGANISM: Artificial Sequence
<220> FEATURE:
<223> OTHER INFORMATION: Synthetic (Fc of Mouse IgG2ab, wherein 231st
      residue of full Mouse IgG2ab is designated as 1st residue)

<400> SEQUENCE: 7

Ala Pro Asp Leu Leu Gly Gly Pro Ser Val Phe Ile Phe Pro Pro Lys
 1               5                  10                  15

Ile Lys Asp Val Leu Met Ile Ser Leu Ser Pro Met Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Leu Arg Val Val Ser Ala Leu Pro Ile Gln His
 65                  70                  75                  80

Gln Asp Trp Met Ser Gly Lys Glu Phe Lys Cys Lys Val Asn Asn Arg
                85                  90                  95

Ala Leu Pro Ser Pro Ile Glu Lys Thr Ile Ser Lys Pro Arg Gly Pro
            100                 105                 110

Val Arg Ala Pro Gln Val Tyr Val Leu Pro Pro Pro Ala Glu Glu Met
        115                 120                 125

Thr Lys Lys Glu Phe Ser Leu Thr Cys Met Ile Thr Gly Phe Leu Pro
    130                 135                 140

Ala Glu Ile Ala Val Asp Trp Thr Ser Asn Gly Arg Thr Glu Gln Asn
145                 150                 155                 160

Tyr Lys Asn Thr Ala Thr Val Leu Asp Ser Asp Gly Ser Tyr Phe Met
                165                 170                 175

Tyr Ser Lys Leu Arg Val Gln Lys Ser Thr Trp Glu Arg Gly Ser Leu
            180                 185                 190

Phe Ala Cys Ser Val Val His Glu Val Leu His Asn His Leu Thr Thr
        195                 200                 205

Lys Thr Ile Ser Arg Ser Leu Gly Lys
    210                 215

<210> SEQ ID NO 8
<211> LENGTH: 217
<212> TYPE: PRT
<213> ORGANISM: Artificial Sequence
<220> FEATURE:
<223> OTHER INFORMATION: Synthetic (Fc of Mouse IgG2b, wherein 231st
      residue of full Mouse IgG2b is designated as 1st residue)

<400> SEQUENCE: 8

Ala Pro Asn Leu Glu Gly Gly Pro Ser Val Phe Ile Phe Pro Pro Asn
 1               5                  10                  15

Ile Lys Asp Val Leu Met Ile Ser Leu Thr Pro Lys Val Thr Cys Val
            20                  25                  30

Val Val Asp Val Ser Glu Asp Asp Pro Asp Val Gln Ile Ser Trp Phe
        35                  40                  45

Val Asn Asn Val Glu Val His Thr Ala Gln Thr Gln Thr His Arg Glu
```

```
        50                  55                  60
Asp Tyr Asn Ser Thr Ile Arg Val Val Ser Thr Leu Pro Ile Gln His
 65                  70                  75                  80

Gln Asp Trp Met Ser Gly Lys Glu Phe Lys Cys Lys Val Asn Asn Lys
                 85                  90                  95

Asp Leu Pro Ser Pro Ile Glu Arg Thr Ile Ser Lys Ile Lys Gly Leu
                100                 105                 110

Val Arg Ala Pro Gln Val Tyr Thr Leu Pro Pro Ala Glu Gln Leu
                115                 120                 125

Ser Arg Lys Asp Val Ser Leu Thr Cys Leu Val Val Gly Phe Asn Pro
        130                 135                 140

Gly Asp Ile Ser Val Glu Trp Thr Ser Asn Gly His Thr Glu Glu Asn
145                 150                 155                 160

Tyr Lys Asp Thr Ala Pro Val Leu Asp Ser Asp Gly Ser Tyr Phe Ile
                165                 170                 175

Tyr Ser Lys Leu Asn Met Lys Thr Ser Lys Trp Glu Lys Thr Asp Ser
                180                 185                 190

Phe Ser Cys Asn Val Arg His Glu Gly Leu Lys Asn Tyr Tyr Leu Lys
                195                 200                 205

Lys Thr Ile Ser Arg Ser Pro Gly Lys
        210                 215

<210> SEQ ID NO 9
<211> LENGTH: 217
<212> TYPE: PRT
<213> ORGANISM: Artificial Sequence
<220> FEATURE:
<223> OTHER INFORMATION: Synthetic (Fc of Mouse IgG3, wherein 231st
      residue of full Mouse IgG3 is designated as 1st residue)

<400> SEQUENCE: 9

Ala Gly Asn Ile Leu Gly Gly Pro Ser Val Phe Ile Phe Pro Pro Lys
  1               5                  10                  15

Pro Lys Asp Ala Leu Met Ile Ser Leu Thr Pro Lys Val Thr Cys Val
                 20                  25                  30

Val Val Asp Val Ser Glu Asp Asp Pro Asp Val His Val Ser Trp Phe
             35                  40                  45

Val Asp Asn Lys Glu Val His Thr Ala Trp Thr Gln Pro Arg Glu Ala
         50                  55                  60

Gln Tyr Asn Ser Thr Phe Arg Val Val Ser Ala Leu Pro Ile Gln His
 65                  70                  75                  80

Gln Asp Trp Met Arg Gly Lys Glu Phe Lys Cys Lys Val Asn Asn Lys
                 85                  90                  95

Ala Leu Pro Ala Pro Ile Glu Arg Thr Ile Ser Lys Pro Lys Gly Arg
                100                 105                 110

Ala Gln Thr Pro Gln Val Tyr Thr Ile Pro Pro Arg Glu Gln Met
                115                 120                 125

Ser Lys Lys Lys Val Ser Leu Thr Cys Leu Val Thr Asn Phe Phe Ser
        130                 135                 140

Glu Ala Ile Ser Val Glu Trp Glu Arg Asn Gly Glu Leu Glu Gln Asp
145                 150                 155                 160

Tyr Lys Asn Thr Pro Pro Ile Leu Asp Ser Asp Gly Thr Tyr Phe Leu
                165                 170                 175

Tyr Ser Lys Leu Thr Val Asp Thr Asp Ser Trp Leu Gln Gly Glu Ile
                180                 185                 190
```

```
Phe Thr Cys Ser Val Val His Glu Ala Leu His Asn His His Thr Gln
            195                 200                 205

Lys Asn Leu Ser Arg Ser Pro Gly Lys
    210                 215
```

PROTEIN IN WHICH ELECTRICAL INTERACTION IS INTRODUCED WITHIN HYDROPHOBIC INTERACTION SITE AND PREPARATION METHOD THEREFOR

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2013/002139, filed Mar. 13, 2014, which claims priority to US Provisional Application No. 61/780,390, filed Mar. 14, 2013, the entire contents of which are incorporated herein by reference.

TECHNICAL FIELD

The present invention relates to heterologous bispecific antibodies (BsAbs) or bispecific fusion proteins (BsFps) with high purity.

BACKGROUND ART

Most of bispecific antibodies (BsAbs) are artificially manufactured to bind two different targets simultaneously rather than generally produced in nature. A double targeting ability provides BsAbs with new applicable field, which has not been managed by monopecific antibodies (MsAbs). Special interest in therapeutic purposes is the provoking possibility, such that BsAbs (1) reliably recruit immune cells into the proximity of target cells, (2) inhibit or activate two distantly apart signaling pathways in target cells to create synergetic effects, and (3) deliver radiation-induced therapeutic substances, medical drugs, toxins or signaling molecules in a specific- and regulatory manner.

BsAbs are generally utilized for delivering T cells to tumor cells in a MHC-independent way, mediating a linkage between cell surface antigens of tumor cells and CD3-TCR complex of cytotoxic T cells (FIG. 1). Catumaxomab(Removab®), rat-mouse hybrid monoclonal antibody, in FIG. 1 is used to treat malignant ascites, which is called "Trifunctional antibody."

Complete chain association should occur at two different levels, in order to produce minimally modified full-length IgG-like BsAbs without any chain association problem. (1) Two heavy chains should be heterologous bispecific, and (2) two light chains (LC) should pair correctly with their respective heavy chains.

Chain association issues should be solved to produce BsAbs in a trustworthy method. As shown in FIG. 2, combination of two heavy chains and two light chains generates 10 different forms of antibody chimera. Among them, only one is a correct BsAb, and the rest are worthless Chimera. This chain association issue reduces production yield of correct BsAb to at least 10 times in industry fields, and causes various problems with difficulties in isolating BsAbs from other chimera. Therefore, many pharmaceutical companies spend a lot of resources and make efforts to develop and obtain technology for producing BsAbs in a direct and reliable way.

Many various BsAb-related techniques (45 different formats) have been developed. These techniques are classified into 4 categories based on the structure. First, heterologous bispecification of heavy chains by various methods comprising structural complementarity kown to Knob-into-Hole or simply KiH, electrostatic steering effect, or CH3 domain shuffling (called to SEEDbody™); second, various antibody fragment formats such as Diabody™, BiTE™ and DART™; third, technology using one or more functional domains combined with intact antibodies, such as Modular Antibody™, Zybody™, dAbs™ and DVD-IG™; and fourth, techniques adopting full length IgG-like scheme as Duobody™ (Fab-Arm Exchange), CrossMab™, Azymetric™, and kI body™ have been developed.

Out of them, Zymeworks through the United States Patent Application No. 2013-892198, claiming a patent for the structure of heteromultimer immunoglobulin chains having mutations in Fc domain, showed that the antibodies of the heterologous multimeric structure could be made by modifying cysteine residues involved in disulfide bonds with charged amino acids.

However, any patent above has not disclosed such a technology that a modified amino acid pair selected from the portion of the hydrophobic interaction induces to selectively couple each other by the electrostatic interaction. The inventors have completed the present invention by confirming that heterologous bispecification takes place more selectively when one pair of amino acids involved in hydrophobic interaction are modified to an acidic amino acid and a basic amino acid, respectively.

SUMMARY OF THE INVENTION

The present invention aims to provide bispecific antibodies with excellent heterologous bispecification (heterodimer).

The other purpose of the present invention is to provide a method for manufacturing proteins that heterologous bispecifications occur well by altering a pair of amino acids in the hydrophobic interactions to the charge opposite to each other For the above object, the first aspect of the present invention is to provide proteins, which the electrostatic interaction has been introduced by the above negative charge and the above positive charge, in that a pair of hydrophobic amino acids selected from the portion of the hydrophobic interaction of the protein, altering one hydrophobic amino acid to a positive charge, and the other hydrophobic amino acid to negative charge. Materials having the positive charge may be basic amino acids may be but not limited to the same, materials having the negative charge may be acidic amino acids but not limited to the same.

The hydrophobic amino acid is any of the amino acid selected from a group consisting of glycine, alanine, valine, leucine, isoleucine, methionine, proline, and phenylalanine, and the acidic amino acid is any one of amino acid selected from a group of aspartic acid or glutamic acid.

Assembly of full-length IgG-like bispecific antibodies from two different HC/LC pairs is made from two chain association processes. In other words, HC heterologous bispecification and productive HC/LC pairing, and their success rates between the two heavy chains, depend on the efficiency of distinguishing between the heavy chain and the light chain.

To find the appropriate variation site, amino acid residues on the hydrophobic interface between the chains of the antibody have been focused since the hydrophobic interaction is the main driving force for folding and binding of the protein. For selecting an appropriate type of modifications as powerful as a hydrophobic interaction, since it provides the discernibility of the protein necessary to solve chain association problem of bispecific antibodies, the electrostatic interaction has been chosen.

Distinction between such chains was conceived to be solved by introducing the complementary pairing of structural modifications at the interface between the two binding chains. One or more hydrophobic amino acids were replaced by mutated charged amino acid to pair with the counterpart. Such a change is hereafter called SHOCAP (substitution of hydrophobic into oppositely charged amino acid pair). SHOCAP in the Fc domain of two the heavy chains generates the positively and negatively charged heavy chains (each called Ha and Hb). These electrostatic interactions prefer a heterologous bispecification (heterodimerization) than homologous bispecification (homodimerization) of the heavy chain. In the same way, modifications of two Fab domains by SHOCAP create positively and negatively charged light chains (called La and Lb, respectively), and the electrostatic interactions with the oppositely charged Fab domains of the heavy chains increase the probability of correct HC/LC pairing.

To produce BsAbs without any chain association problem, two independent modifications were introduced into naturally-occurring antibodies. One is for heterologous bispecification of the Fc domain and the other for the correct pairing of the heavy chain and the light chain.

In the present invention, heterologous bispecification (heterodimerization) of the Fc domain occurs firmly and actively if one or more hydrophobic interactions in the Fc domain of the antibody are converted to electrostatic pair interactions (for example, conversion of the hydrophobic interaction of two tyrosines at the 407th residues (Y407: Y407) to the electrostatic pair interaction of aspartate and lysine the 407th residues (D407: K407)).

The use of the SHOCAP technology can easily distinguish two heavy chains (heavy chain) and two light chains (light chain) when major hydrophobic residues of the Fab domain was substituted (for example, leucine of the 128th residue and phenylalanine of the 118th residue (L128: F118) to lysine of the 128th residue and aspartic acid of the 118th residue (K128: D118). Therefore, IgG-like bispecific antibodies can be generated by applying SHOCAP technology to the Fc and Fab domains of antibodies.

The second aspect of the present invention is to provide antibodies in which the electrostatic interaction has been introduced into the region of the hydrophobic interaction by mutating one hydrophobic amino acid to a positively charged amino acid and the other to a negative charge. The above positive charge may be basic but not limited to the same and the above negative charge may be acidic but not limited to the same.

Specifically, antibodies have binding forces by electrostatic interactions between any one of the amino acid mutated to an acidic amino acid selected from aspartic acid or glutamic acid, and the other to a basic amino acid selected from lysine, arginine, or histidine, of which mutations were introduced to one or more amino acid pairs selected from the group of amino acid pairs, consisting of 351 leucine and 351 leucine pair, 395 proline and 397 valine pair, 395 proline and 395 proline pair, 407 tyrosine and 407 tyrosine pair of hydrophobic interaction in CH3 domain; and 128 leucine and 118 phenylalanine pair, 128 leucine and 133 valine pair, 141 alanine and 116 phenylalanine pair, 141 alanine and 135 leucine pair, 145 leucine and 133 valine pair, 170 phenylalanine and 135 leucine pair, 185 valine and 118 phenylalanine pair and 185 valine and 135 leucine pair between CH1 domain and CL domain of human antibody. More specifically, antibodies are characterized to be mutated on a set of combination selected from the group consisting of Z0 to Z14 in Table 4. The antibodies can have a pair of ectodomains with a pair of functions. The ectodomain can play a role in cancer and signaling, and this toxin may be used to treat cancer coupling cell death bound by another specific antibody. The ectodomains may be a pair of ectodomains selected from the group consisting of TNR2, Her3, Tie2, TGFbR1, BMPbR1, Il-12R-b1, IL-4Ra, ITGA4, ITGA2B, INFAR1, IL-12A, IL-4, InFa, BMP2, IL-1R1L, IL-17RA, IL-17A, Fas, FltD2, Her1, Tie1, TGFbR2, IL-12R-b2, IL-13Ra1, ITGB1, ITGB3, INFAR2, IL-12B, IL-13, INFb, BMP7, IL-1RAP , IL-17RC, and IL-17F, but not limited to the same. More specifically, the antibodies may be fused with a combination of ectodomains selected from a combination group consisting of Her2/FltD2 combination, Her1/Her3 combination, and Tie/Tie2 Ectoin. More specifically, it may be bispecific antibodies having the heavy chain mutated to Z14 combination and the light chain simultaneously including 4D9 ectodomain specific for A-type influenza virus and 2B9 ectodomain specific for B-type influenza virus. More specifically, the above antibodies may be the antibodies with enhanced pairing between the heavy and the light chains, consisting of any combination selected from a combination group consisting of V1 to V5, W1 to W8, V2p, V3p, W4p, V3W4, W4v3, and V3v1 of one heavy chain (HP) and the other the heavy chain (HN), and one light chain (LP) and the other light chain (LN) shown in Table 7. More specifically, the above antibodies may be the antibodies with enhanced pairing between the heavy chain and the light chain, consisting of tryptophan-to-lysine mutant at the 103th residue, lysine-to-aspartic acid mutant at the 128th residue, phenylalanine-to-lysine mutant at the 118th residue, proline-to-aspartic acid mutant at the 44th residue.

The third aspect of the present invention is to provide the method of manufacturing proteins of which chain selectivity has been increased, comprising of the steps such as;

(1) selecting a pair of hydrophobic amino acids in the region of the hydrophobic interaction between the polypeptide chain and the polypeptide chain;
(2) modifying one hydrophobic amino acid to a positive charge, and the other hydrophobic amino acid to a negative charge in the selected pair of amino acids; and
(3) binding by the electrostatic interactions through contacting between the positive and negative charges. Material having the positive charge may be a basic amino acid but not limited to the same, and material having the negative charge may be an acidic amino acid but not limited to the same.

A fourth aspect of the present invention is to provide a method for measuring the extent of pairing between the heavy chain and the light chain of BsAbs using BsAbs having the heavy chain mutated to the Z14 combination and the common light chain including 4D9 ectodomain specific for A-type influenza virus and 2B9 ectodomain specific for B-type influenza virus.

SHOCAP modifications of the heavy chain of the Fc domain create the positively and negatively charged heavy chain (called Ha and Hb each hereinafter). These electrostatic interactions prefer heterologous bispecification (heterodimerization) than homologous bispecification (homodimerization) of the heavy chain. In the same way, SHOCAP modifications of two Fab domains generate the positively and negatively charged light chains (called La and Lb, respectively). And the electrostatic interaction of oppositely charged Fab domain of the heavy chain increases the probability of correct HC/LC pairing. Accordingly, the antibodies in the present invention can obtain heterologous bispecific antibodies or proteins which are less contaminated with homodimers or monomers.

Another advantage of the present invention is to induce less immune rejection since mutations on minimal number of amino acids have not caused any significant structural changes of natural antibodies, and further target residues have been buried deep in the surface of hydrophobic interaction between the heavy and light chains.

DESCRIPTION OF DRAWINGS

FIG. 4 shows that the amino acid sequences are highly conserved in the Fc domains of antibodies between human IgG1-IgG4 (SEQ ID Nos 1-4, respectively) and mouse IgG1-IgG3 (SEQ ID Nos 5-9, respectively).

FIG. 9 is SDS-PAGE analysis of comparing the efficiency of heterologous bispecifications between heterologous Her3/FltD2 BsAbs and control antibodies which are generated based on the Z14. A) schematic diagram of a heterologous BsAb, B) SDS-PAGE analysis FIG. 10 compares the efficiency of heterologous bispecifications between heterologous Her1/Her3 BsAb and control antibody which are generated based on the Z14. (A) schematic diagram of a heterologous BsAb, Her1/Her3, (B) SDS-PAGE analysis, (C) HIC-HPLC analysis FIG. 11 compares the efficiency of heterologous bispecifications between heterologous Tie1/Tie2 BsAb and control antibody which are generated based on the Z14. (A) schematic diagram of a heterologous BsAb, Tie1/Tie2, (B) SDS-PAGE analysis, (C) HIC-HPLC analysis

DETAILED DESCRIPTION

Hereinafter, the present invention will be described in further detail with reference to examples. It is to be understood, however, that these examples are for illustrative purposes only and are not to be construed to limit the scope of the present invention.

EXAMPLE 1

Heterodimerization of the Fc Domain

A) Selection of Modification Sites and Types

Figure 1:
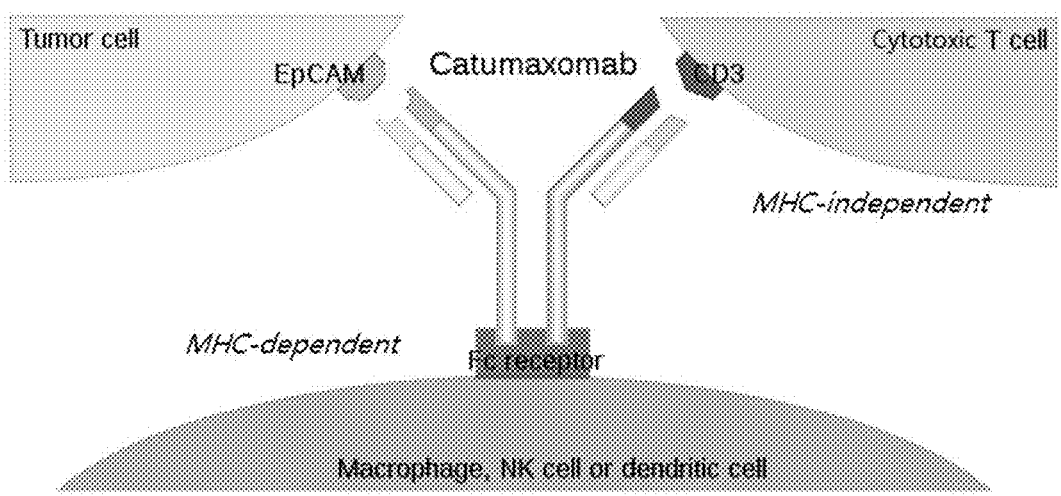
FIG. 1 shows a general form of Bispecific Antibody. As an example, Catumaxomab (Removab®) rat-mouse hybrid monoclonal antibody is used to treat malignant ascites.
Figure 2:
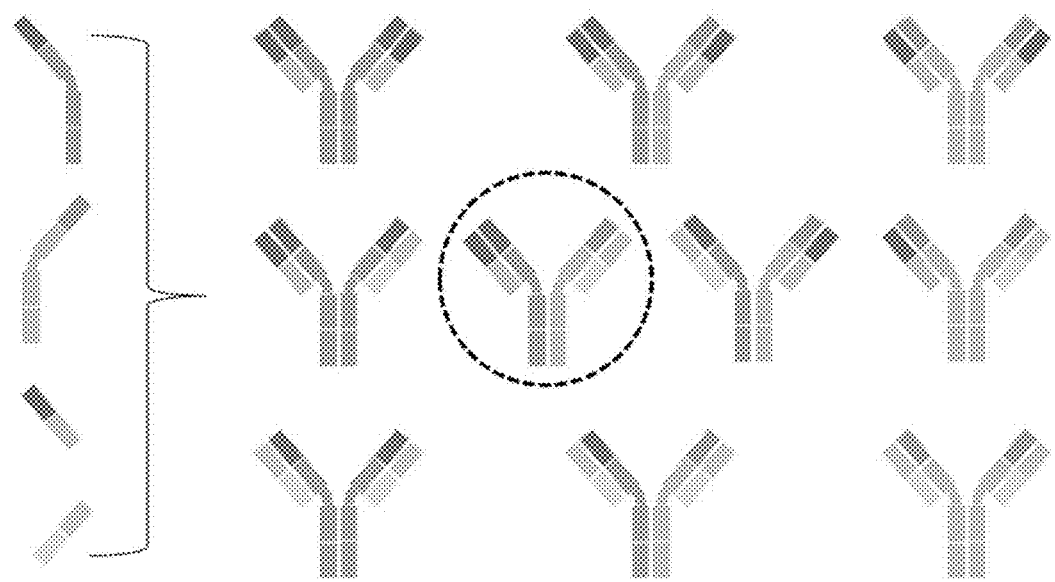
FIG. 2 shows that a combination of two light chains and two heavy chains generates 10 different antibody chimera.
Figure 3:
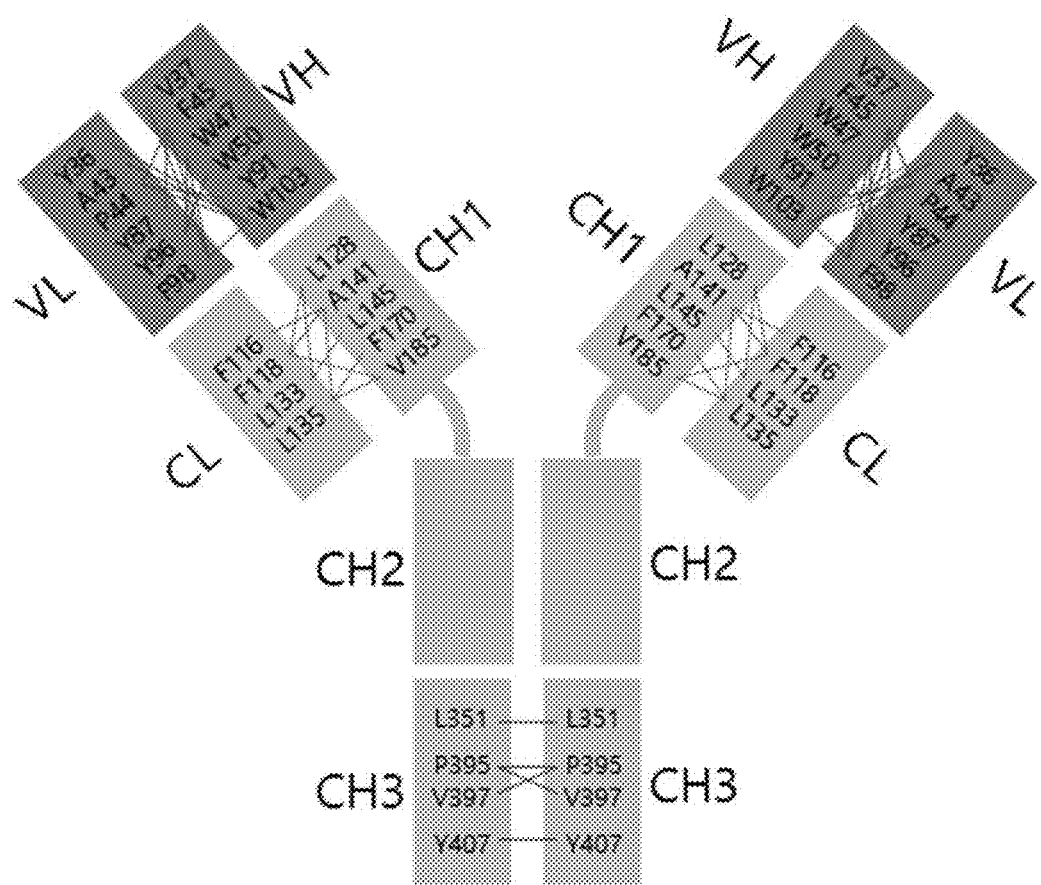
FIG. 3 shows amino acids which are involved in hydrophobic interactions of antibodies.

To search for the appropriate sites of SHOCAP modification in both Fc and Fa, hydrophobic contacts between the antibody chains were analyzed by Protein Interaction Calculator (PIC). A number of hydrophobic interactions between the chains have been found throughout the entire antibody domains. Five pairs of residues in two CH3 domains were involved in the hydrophobic interactions between the chains (see Table 1 and FIG. 3). Three hydrophobic interactions at different sites in the two CH3 domains were distributed symmetrically. One region is made of mutual hydrophobic interactions between P395 and V397, and the other two regions are made of the interaction of a hydrophobic pair of Y407 and L351, respectively. These residues in SEQ ID NO: 1-9 were found to be highly conserved between human and mouse (and also other mammals) antibody classes (FIG. 4), indicating that these hydrophobic pair interactions might be pivotal in maintaining the dimeric structural integrity of the Fc domains. Nine pairs of residues are involved in the hydrophobic interactions between CH1 and CL (Table 2, FIG. 3). Except in the case of residues in the CDR, a total of 12 pairs of residues from the VH and VL domains were involved in hydrophobic interactions between the chains (see Table 3 and FIG. 3). No notable interaction exists in the interface between CH2-CH2 domain.

TABLE 1

| HIP No. | CH3 Domain (Chain A) | CH3 Domain (Chain B) |
|---|---|---|
| 1 | L351 | L351 |
| 2 | P395 | V397 |
| 3 | P395 | P395 |
| 4 | V397 | P395 |
| 5 | Y407 | Y407 |

TABLE 2

| HIP No. | CH1 Domain | CL Domain |
|---|---|---|
| 6 | L128 | F118 |
| 7 | L128 | V133 |
| 8 | A141 | F116 |
| 9 | A141 | F118 |
| 10 | A141 | L135 |
| 11 | L145 | V133 |
| 12 | F170 | L135 |
| 13 | V185 | F118 |
| 14 | V185 | L135 |

TABLE 3

| HIP No. | VH Domain | VL Domain |
|---|---|---|
| 15 | V37 | F98 |
| 16 | F45 | P44 |
| 17 | F45 | Y87 |
| 18 | F45 | F98 |
| 19 | W47 | Y96 |
| 20 | W47 | F98 |
| 21 | W50 | Y96 |
| 22 | Y91 | P44 |
| 23 | W103 | Y36 |
| 24 | W103 | Y36 |
| 25 | W103 | A43 |
| 26 | W103 | P44 |
| 27 | W103 | F98 |

To solve problems with chain association in the heterologous bispecification of Fc, five pairs of residues consisting of four other hydrophobic residues (L351, P395, V397 and V407) that span the two CH3 domains have been considered as major modification sites.

Figure 5:
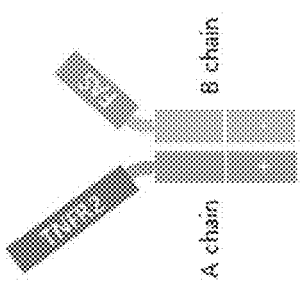
FIG. 5 shows 14 sets of mutations in the Fc portion bound by respective TNFR2 ectodomain and FAS ectodomain, which introduced the electrostatic interactions, in order to show the efficiency of heterologous bispecification. Positively charged amino acids were inserted into the regions of hydrophobic interactions in chain A and, negatively charged amino acids was inserted into the regions of hydrophobic interactions in chain B.
Figure 6:
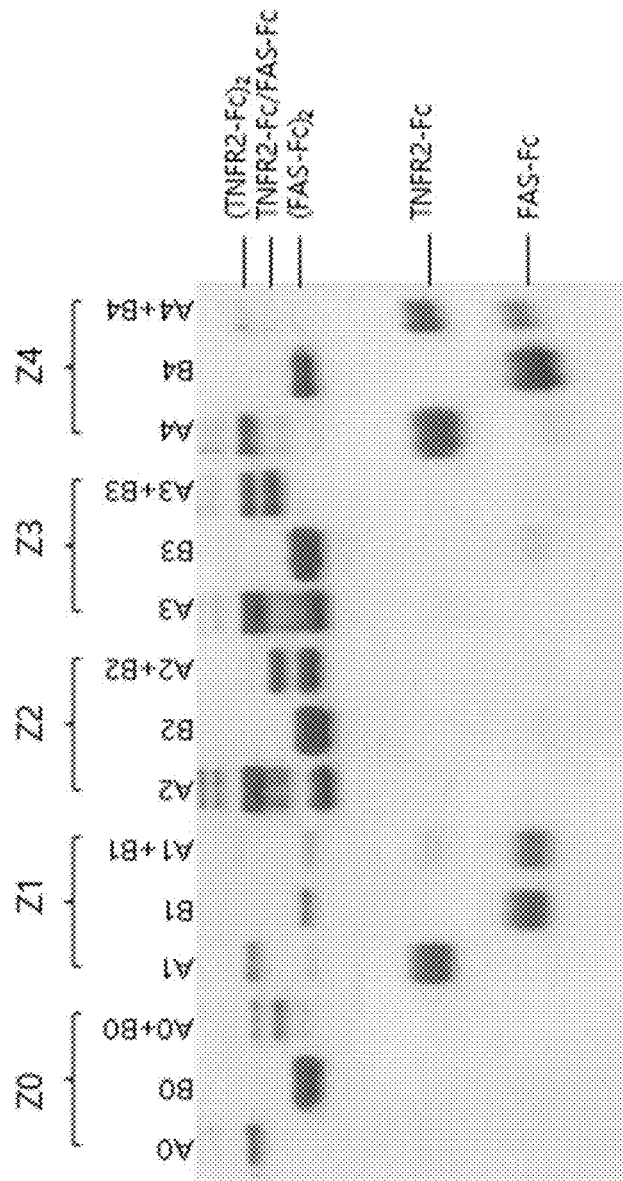
FIG. 6 shows how well heterologous bispecifications of Fc occur in the set of Z0 to Z4 in Table 4 by SDS-PAGE analysis.

The four hydrophobic residues (L351, P393, V397 and Y407) are transformed, each or in combination, into electrostatic interaction pairs to produce a total of 14 sets of TNFR2-Fc and FAS-Fc variants (Table 4 and FIG. 5).

TABLE 4

| Set No. | Chain A (TNFR2) | | Chain B (FAS) | |
|---|---|---|---|---|
| Z0 | A0 | — | B0 | — |
| Z1 | A1 | L351K | B1 | L351D |
| Z2 | A2 | P395K | B2 | P395D |
| Z3 | A3 | Y407K | B3 | Y407D |
| Z4 | A4 | L351K/P395K | B4 | L351D/P395D |
| Z5 | A5 | L351K/Y407K | B5 | L351D/Y407D |
| Z6 | A6 | T394K/P395K | B6 | T394D/P395D |
| Z7 | A7 | T394K/V397K | B7 | T394D/V397D |
| Z8 | A8 | P395K/V397K | B8 | P395D/V397D |
| Z9 | A9 | P395K/Y407K | B9 | P395D/Y407D |
| Z10 | 1A10 | L351K/T394K/P395K | B10 | L351D/T394D/P395D |
| Z11 | 1A11 | L351K/T394K/V397K | B11 | L351D/T394D/V397D |
| Z12 | 1A12 | L351K/P395K/V397K | B12 | L351D/P395D/V397D |
| Z13 | 1A13 | L351K/P395K/Y407K | B13 | L351D/P395D/Y407D |
| Z14 | 1A14 | L351K/T394K/P395K/V397K | B14 | L351D/T394D/P395D/V397D |

The potential of heterologous bispecification of those 14 sets of the mutants was examined using SDS-PAGE analysis. In order to facilitate the interpretation of the results, two receptors having ectodomains with different molecular size and distinct ligand-binding activity were selected. The hydrophobic moiety in these large Fc ectodomains of TNFR2 capable of binding to TNFα was mutated to the positively charged moiety (called "A chain" hereinafter). The hydrophobic moiety in these small Fc ectodomains of FAS having a binding affinity for FASL was substituted to the negatively charged moiety (called "B chain" hereinafter).

Figure 7:
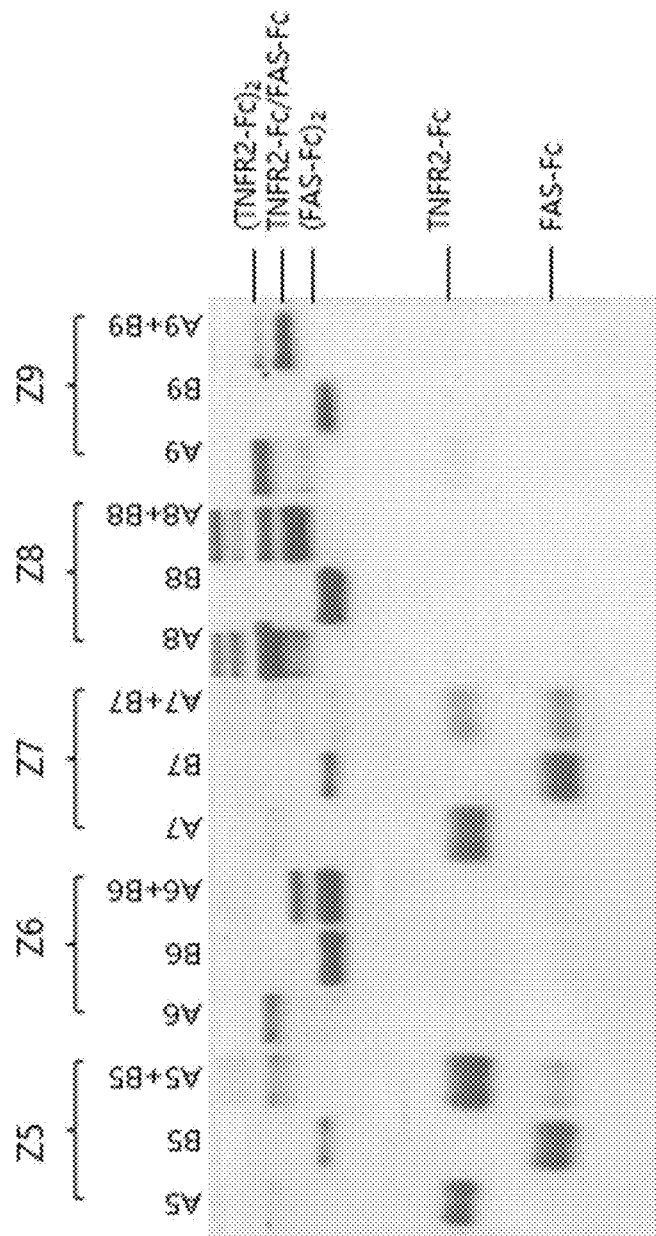
FIG. 7 shows how well heterologous bispecifications of Fc occur in the set of Z5 to Z9 in Table 4 by SDS-PAGE analysis.
Figure 8:
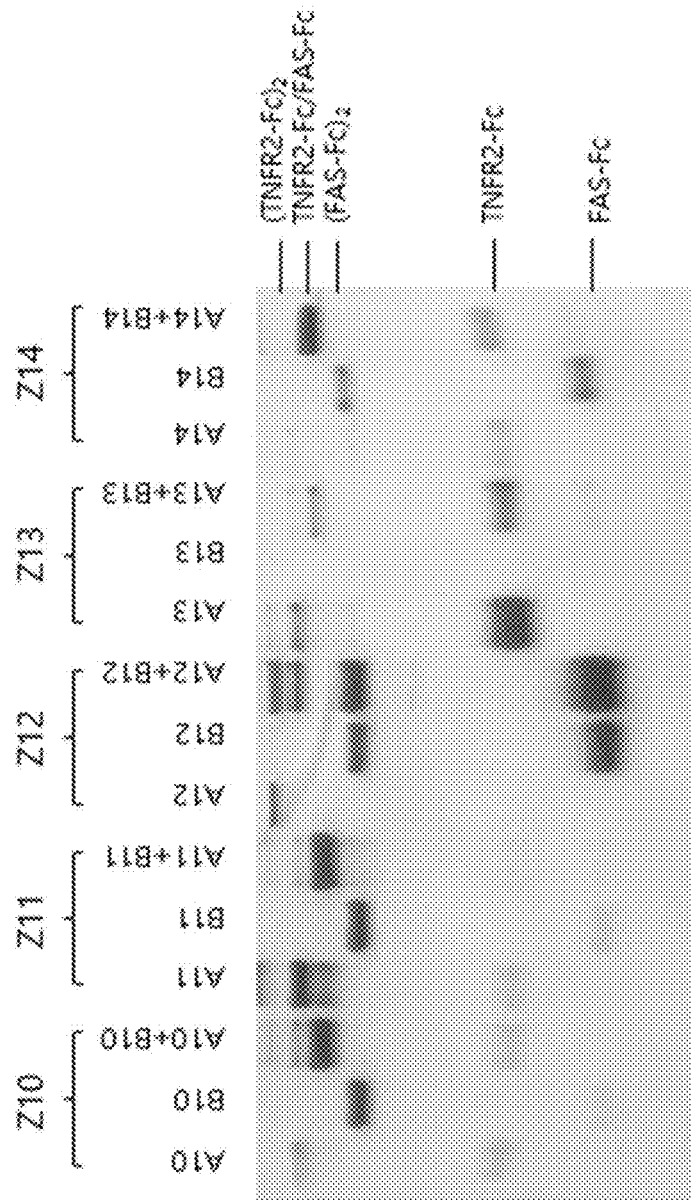
FIG. 8 shows how well heterologous bispecifications of Fc occur in the set of Z10 to Z14 in Table 4 by SDS-PAGE analysis.

In each of the variants set, A and B chains were independently expressed at the same time. Fc fusion proteins produced from sets of single (A and B) and coexpression (A+B) have been purified by protein A chromatography. Proteins were finally eluted with 1 ml of protein A elution buffer solution, 10 µl out of eluted protein fractions were analyzed by 10% SDS-PAGE. The possibility of the heterologous bispecification was determined by comparing the band density of heterologous bispecific TNFR2-Fc/FAS-Fc with that of homologous bispecific (TNFR2-Fc)$_2$ and (FAS-Fc)$_2$ in the coexpression setting (A+B). In addition, monomeric TNFR2-Fc and FAS-Fc products were compared with homologous bispecific (TNFR2-Fc)$_2$ and (FAS-Fc)$_2$ products in the set of single expression (A and B). FIG. 7 shows the data set of Z5-Z9 variants. FIG. 8 shows the data set of Z10-Z14 variants. A set of Z14 mutant was finally selected as the best set. The probability of the heterologous bispecification of Z14 variant was likely better than any others. In this set, heterologous bisepcific TNFR2-Fc/FAS-Fc was the most excellent compared to homologous bispecific (TNFR2-Fc)2 and (FAS-Fc)$_2$ in the set of coexpression, and monomeric TNFR2-Fc and FAS-Fc products were the most unstable in the set of single expression. It shows that the antibodies in accordance with the present invention are less contaminated with monomeric or homologous bispecific variants.

EXAMPLE 2

Preparation of Heterologous BsAbs Based on Z14 in Table 4

By employing heterologous bispecification of Fc domains based on Z14, a total of 17 different heterologous bispecific Fc fusion proteins (BsFcFs) for various target diseases in Table 5.

TABLE 5

| | Fc Origin | A Chain | B Chain | Target Diseases |
|---|---|---|---|---|
| I | Human (G1) | TNFR2 | Fas | Autoimmune Diseases |
| II | Human (G1) | Her3 | Flt1D2 | Cancer |
| III | Human (G1) | Her3 | Her1 | Cancer |
| IV | Human (G1) | Tie2 | Tie1 | Cancer |
| V | Human (G1) | TGFbR1 | TGFbR2 | Fibrosis, Wound healing and Cancer |
| VI | Human (G1) | BMPbR1 | BMPbR2 | Osteopetrosis |
| VII | Human (G1) | IL-12R-b1 | IL-12R-b2 | Autoimmune Diseases (Psoriasis, MS and Crohn) |
| VIII | Human (G1) | IL-4Ra | IL-13Ra1 | Asthma and Atopy |
| IX | Human (G1) | ITGA4 | ITGB1 | MS |
| X | Human (G1) | ITGA2B | ITGB3 | Thrombosis |
| XI | Human (G1) | INFAR1 | INFAR2 | Autoimmune Diseases |
| XII | Human (G2) | IL-12A | IL-12B | Immunotherapeutic anticancer agent |
| XIII | Human (G2) | IL-4 | IL-13 | Autoimmune Diseases (Psoriasis, MS and Crohn) |
| XIV | Human (G2) | INFa | INFb | Cander, Hepatocarcinoma, MS |
| XV | Human (u/dG2) | BMP2 | BMP7 | Osteopetrosis |
| XVI | Human (E) | IL-1R1L | IL-1RAP | Atopy (anti IL-33 blocker) |
| XVIII | Human (G1) | IL-17RA | IL-17RC | Autoimmune Diseases (Psoriasis, MS and Crohn) |
| XIV | Human (u/dG2) | IL-17A | IL-17F | Immunotherapeutic anticancer agent |

A. Design for Heterologous Bispecific Her3/FltD2 Based on Z14

Her3 ectodomain was fused to the positively charged Fc domain (A chain; 97 kD), and FltD2 domain was to the negatively charged (B chain, 40 kD). Positive extracellular domains have been reported to retain the possibility of inherent homologous bispecification.

SDS-PAGE Patterns

Two matched chains were co-expressed, purified by protein A chromatography, and analyzed by 10% SDS-PAGE. Z14 heterologous bispecification was superior to others since monomeric Her3-Fc and FltD2-Fc were seen in the three different control sets but not in Z14.

B. Design for Heterologous Bispecific Her1/Her3 Based on Z14

Her3 ectodomain was fused to the positively charged Fc domain (A chain; 97 kD), and Her1 domain was to the negatively charged (B chain, 95 kD). Positive extracellular domains have been known to maintain the possibility of inherent homologous bispecification.

(1) SDS-PAGE Pattern

Figure 10:
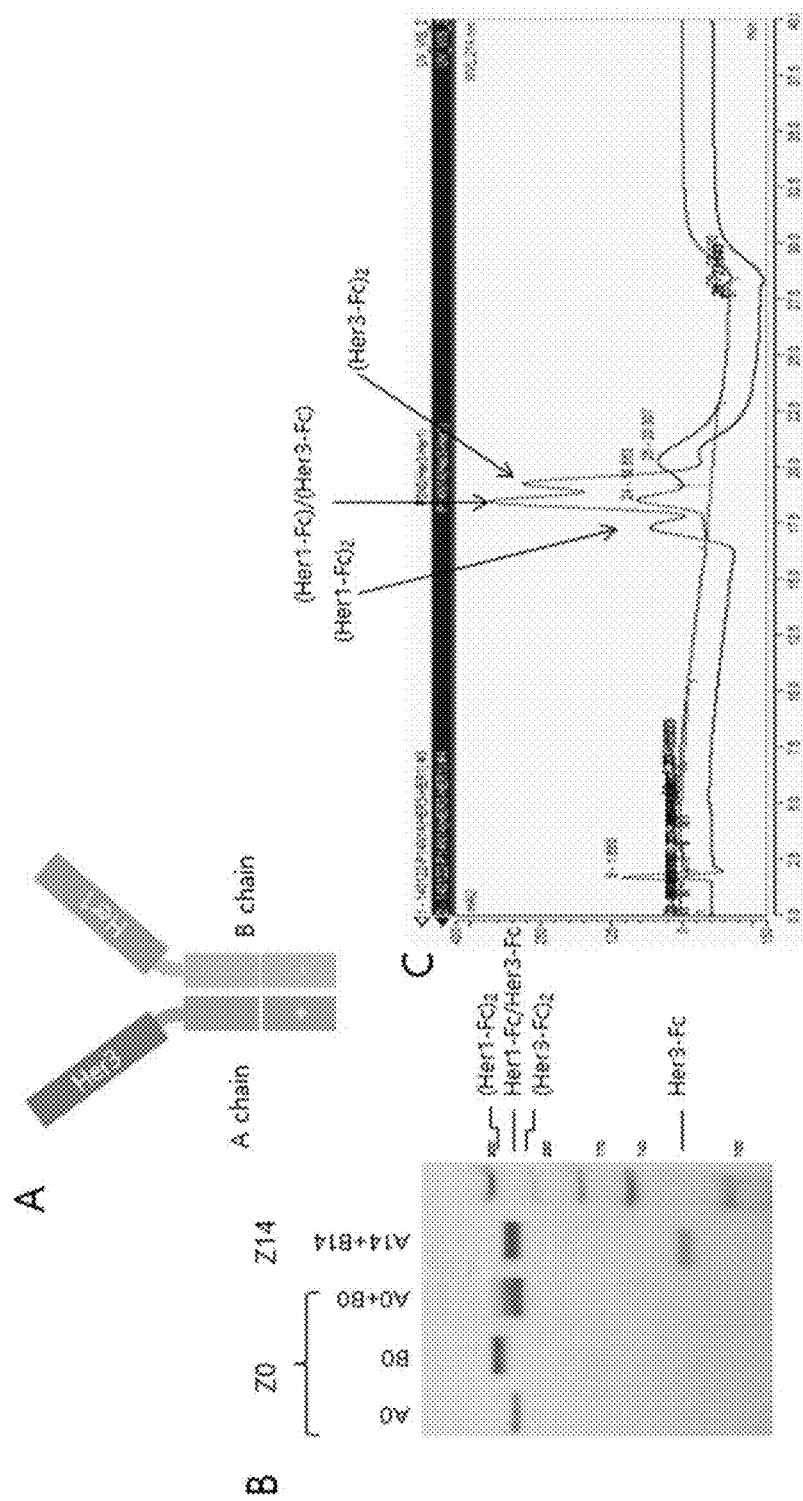

Two matched chains were co-expressed, purified by protein A chromatography, and analyzed by 10% SDS-PAGE. The possibility of Z14 heterologous bispecification was high enough to overcome inherent homologous bispecification of Her1 and Her3 although monomeric Her3-Fc and Her1-Fc forms were seen in Z0 set (FIG. 10 (B)).

(2) HIC-HPLC Analysis

20 μl of the concentrated sample (1~5mg/ml) was loaded onto TSK gel phenyl HIC column. Linear gradient from 60 to 100% acetonitrile was applied with a flow rate of 0.1 ml/min for 40 minutes. Observation was carried out at 214 and 280 nm. Similar to the SDS-PAGE pattern, Z14 showed a high potential for heterologous bispecification (see FIG. 10 (C)).

C. Design for Heterologous Bispecific Tie/Tie2 Based on Z14

Tie1 ectodomain was fused to the positively charged Fc domain (A chain), and Tie2 domain was to the negatively charged (B chain).

(1) SDS-PAGE Pattern

Figure 11:
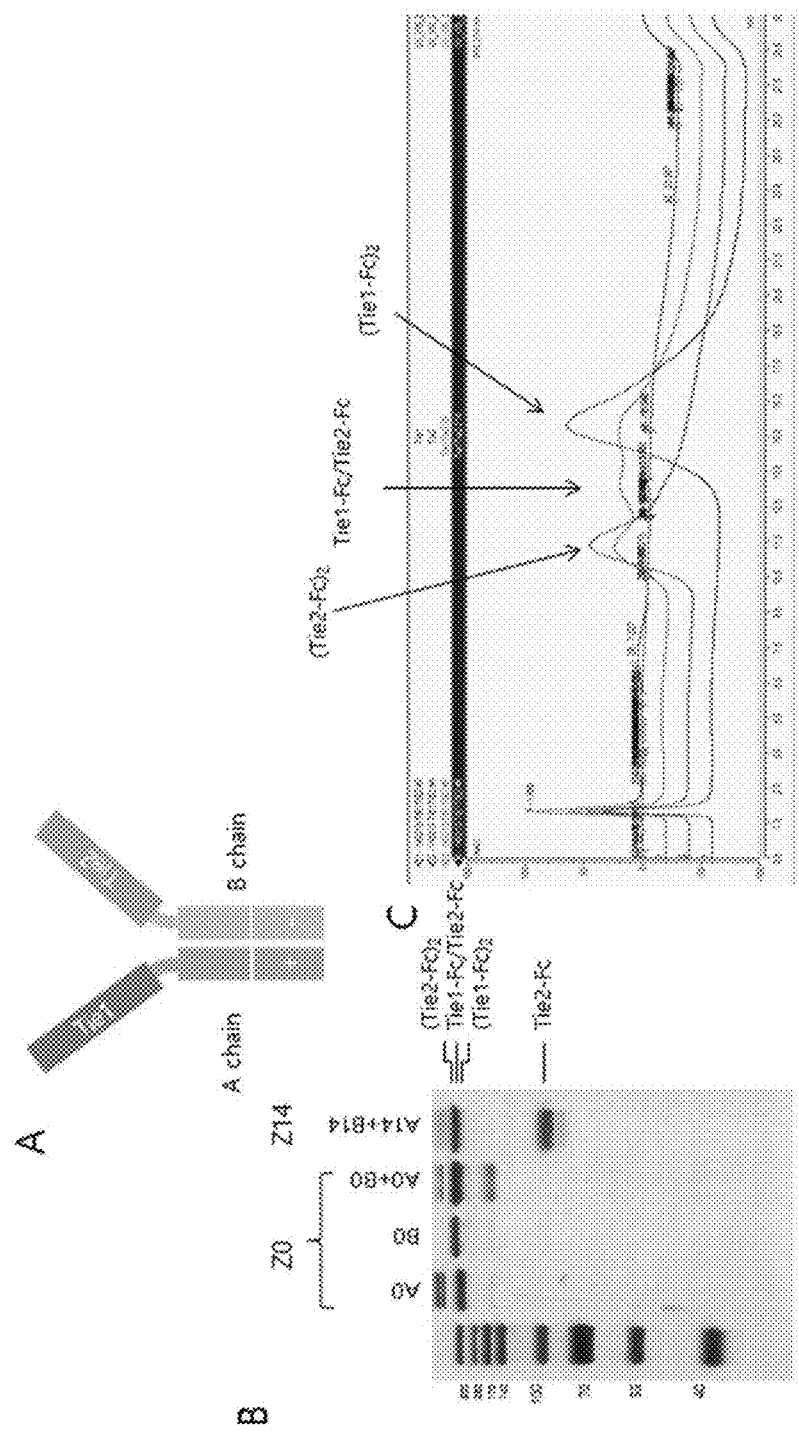

Two matched chains were co-expressed, purified by protein A chromatography, and analyzed by 10% SDS-PAGE. Monomeric Tie1-Fc and Tie2-Fc forms were seen in Z0 set but not in Z14. It indicates that Z14 retains the excellent potential for heterologous bispecification (see FIG. 11 (B)).

(2) HIC-HPLC Analysis

The HIC-HPLC analysis was performed as described previously. Similar to the SDS-PAGE pattern, it indicates that a potential for heterologous bispecification of Z14 is high (see FIG. 11 (C)).

EXAMPLE 3

Preparation of Heterologous BsAbs from Antibodies having Common Light Chains

Figure 12:
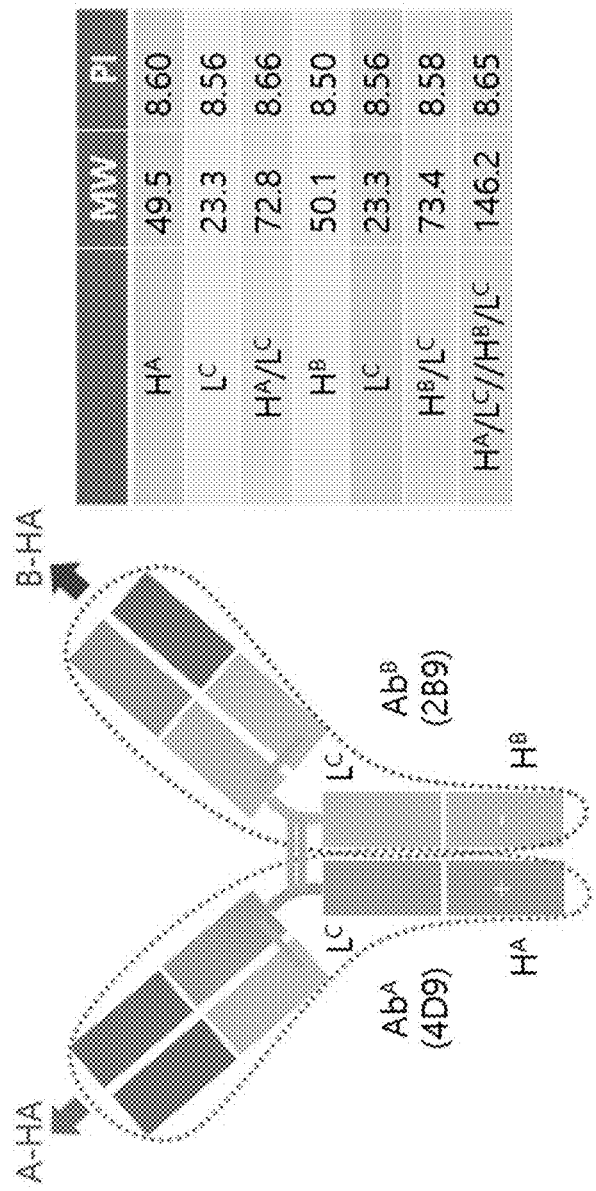
FIG. 12 shows heterologous bispecification to share a common light chain of the antibody. BsAbs are only made possible by the heterologous bispecification of Fc because it does not need correct pairing of the heavy chain and light chains.

Two fully humanized antibodies have been found by the technique of phage display. One is 4D9, specific for A-type influenza virus, and the other is 2B9, specific for B-type influenza virus. Interestingly, it has been found that the two antibodies share a single common light chain (see FIG. 12). A common light chain bispecific antibody (CLC-BsAb) was designed using the benefits of sharing the common light chain in the two antibodies. Dual specific antibodies may be formed only by Fc heterologous bispecification (that is, the process of correct pairing of HC/LC can be omitted).

Figure 13:
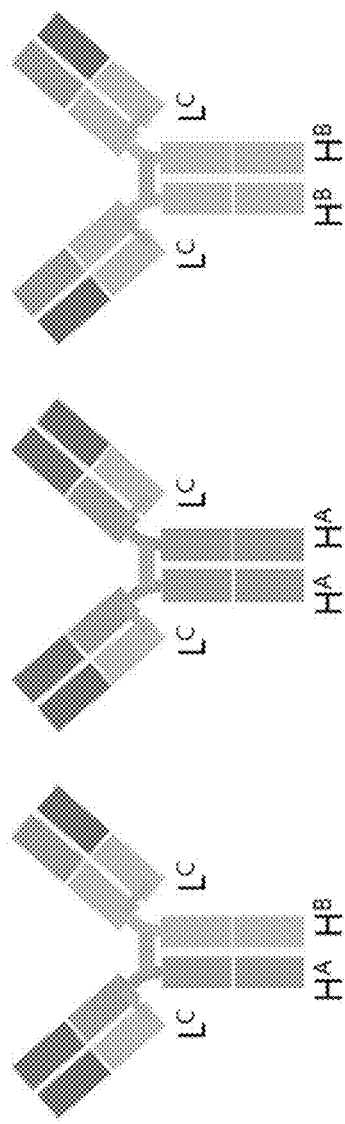
FIG. 13 is a schematic diagram showing that 3 types of antibodies, but not the 10 types, are made in the case of antibodies sharing a common light chain

When natural two heavy pairs with a common light chain, three (not 10) possible antibodies are produced (see FIG. 13). Three control sets and Z14 set were made as shown in Table 6.

TABLE 6

| Set | HA | | HB | | LC |
|-----|-----|-----|-----|-----|-----|
| Z0 | HA0 | — | HB0 | — | — |
| Z14 | HA14 | L351K/T394K/P395K/V397K | HB14 | L351D/T394D/P395D/V397D | — |
| CPC | HPC | D399K/E356K | HNC | K409D/K392D | |
| KiH | HKC | T366S/L368A/Y407V | HHC | T366W | |
| AzS | HAC | T350V/T366L/K392L/T394W | HBC | T350V/L351Y/F405A/Y407V | |

(1) Analysis of Result

Figure 14:
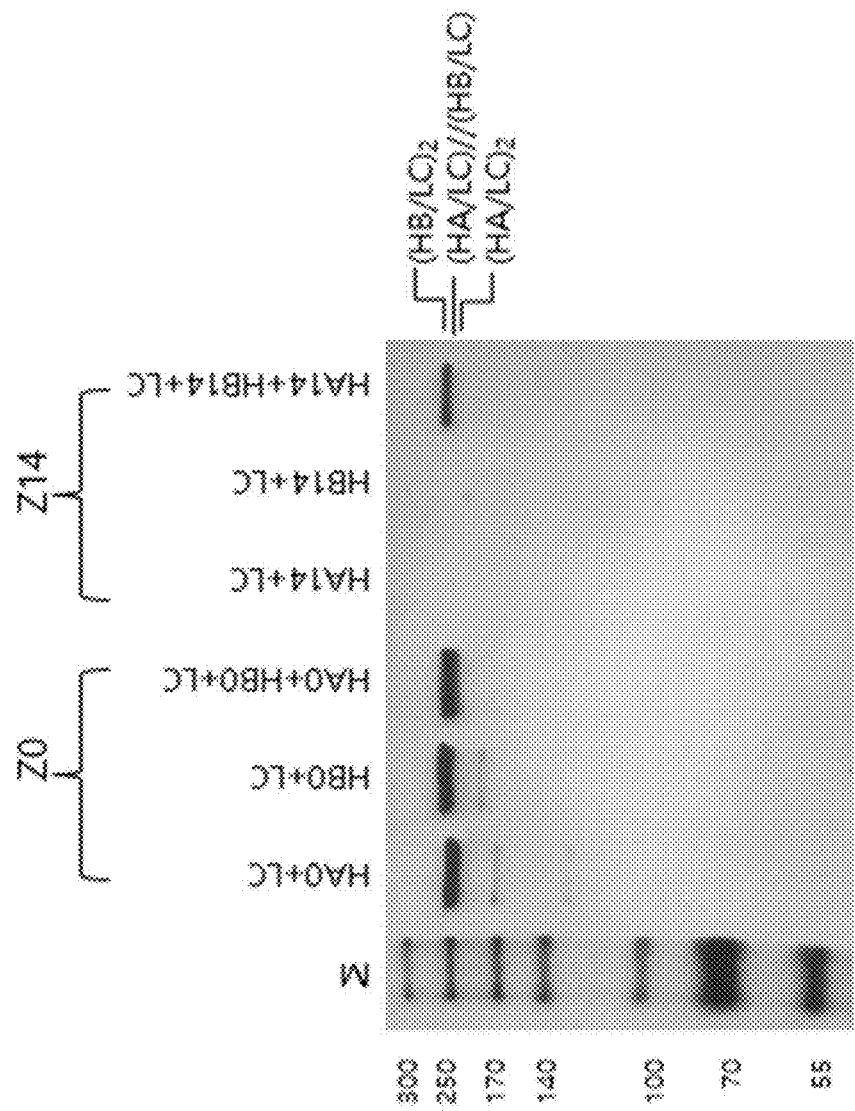
FIG. 14 shows that, from a view as a result of the result of SDS-PAGE analysis, BsAbs are purely produced in the case of antibodies of sharing the common light chains prepared based on the Z14 in Table 4.

As expected, a natural set (Z0) generated the three possible antibodies in SDS-PAGE analysis. (HB/LC)$_2$, (HA/LC)//(HB/LC) and (HA/LC)$_2$. In contrast, Z14 set only produced bispecific forms (HA/LC)//(HB/LC) (see FIG. 14). Z14 set did not produce monomeric antibodies at any visible levels. It reveals that the samples co-expressed by Z14 set is not contaminated with monomeric antibodies and is highly pure with only bispecific antibody forms.

Figure 15:
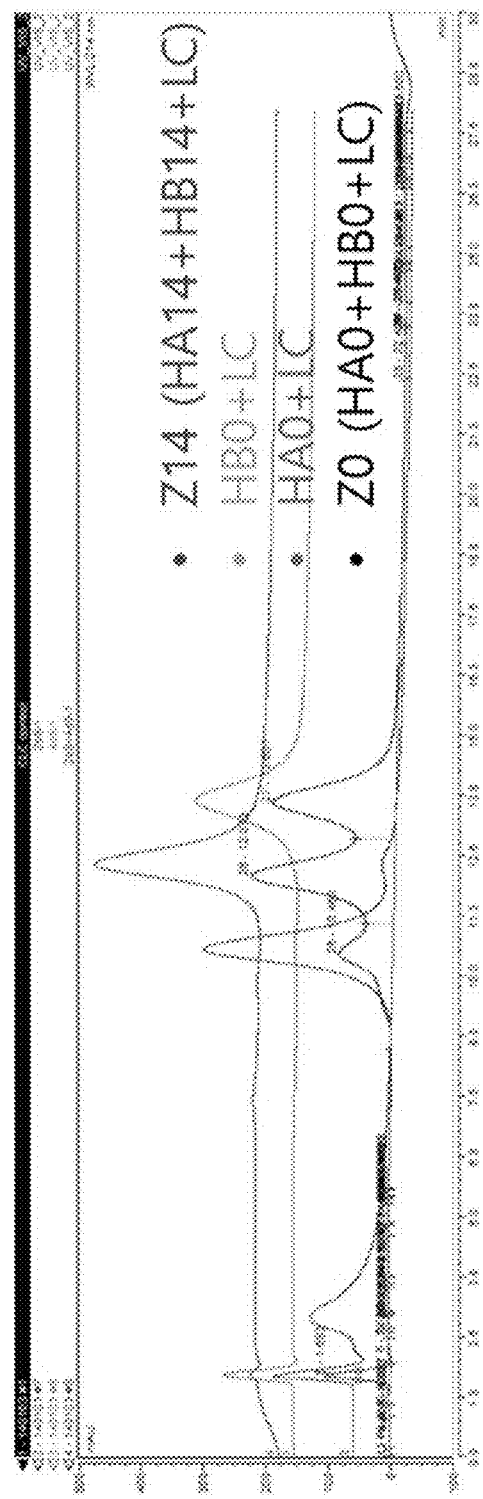
FIG. 15 shows that, from a view as a result of the result of HIS-HPLC chromatography, BsAbs are purely produced in the case of antibodies of sharing the common light chains prepared based on the Z14 in Table 4.

(2) HIC Analysis Purity of Z14 was evaluated by HIC-HPLC chromatography. Z0 set has three peaks corresponding to each (HA/LC)$_2$, (HA/LC)//(HB/LC) and (HB/LC)$_2$. In contrast, Z14 set has a single peak corresponding to bispecific (HA/LC)//(HB/LC) antibodies. It reveals that, similar to the SDS-PAGE result, the samples co-expressed by Z14 set is not contaminated with monomeric antibodies and is highly pure with only bispecific antibody forms (see FIG. 15).

(3) Confirmation of Dual Antigen-Binding Activity

Two antigens, A-HA5 and B-HA, were separately coated in three different amounts (100, 50 and 25 ng/well) on the ELISA plate. After blocking with blocking solution, 100 ng of the antibody was added and incubated overnight. The plate was thoroughly washed, and HRP-conjugated anti-human Fc mouse antibody was added to each well.

Result Analysis

Figure 16:
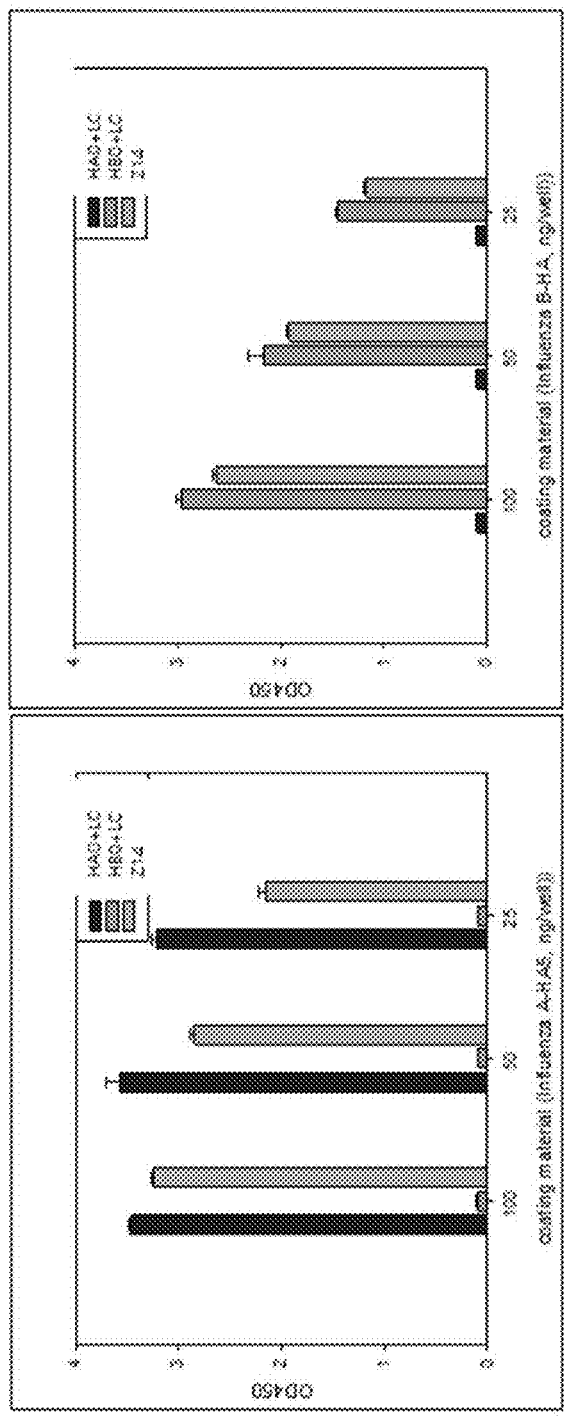
FIG. 16 shows that the antibodies produced based on the Z14 in Table 4 have bispecific antigen-binding activity. 4D9 (HA0+LC) and 2B9 (HB)+LC) were used as control.

Z14 has dual binding activity against both A-HA5 and B-HA antigens. On the other hand, the two control antibodies of 4D9 (HA0+LC) and 2B ((HB0+LC) showed single binding activity (see FIG. 16).

EXAMPLE 4

Measurement of the Receptor Binding Activity of the Fc Domain of Antibodies 100 ng of FcRn-Fc fusion proteins were coated in each well of the ELISA plate. After blocking with blocking solution, 100 ng of 4D9 (HA0+LC), 2B9 (HB0+LC), and Z14 antibodies were added and incubated overnight. The plate was thoroughly washed, and HRP-conjugated anti-human Fc mouse antibody was added to each well.

Figure 17:
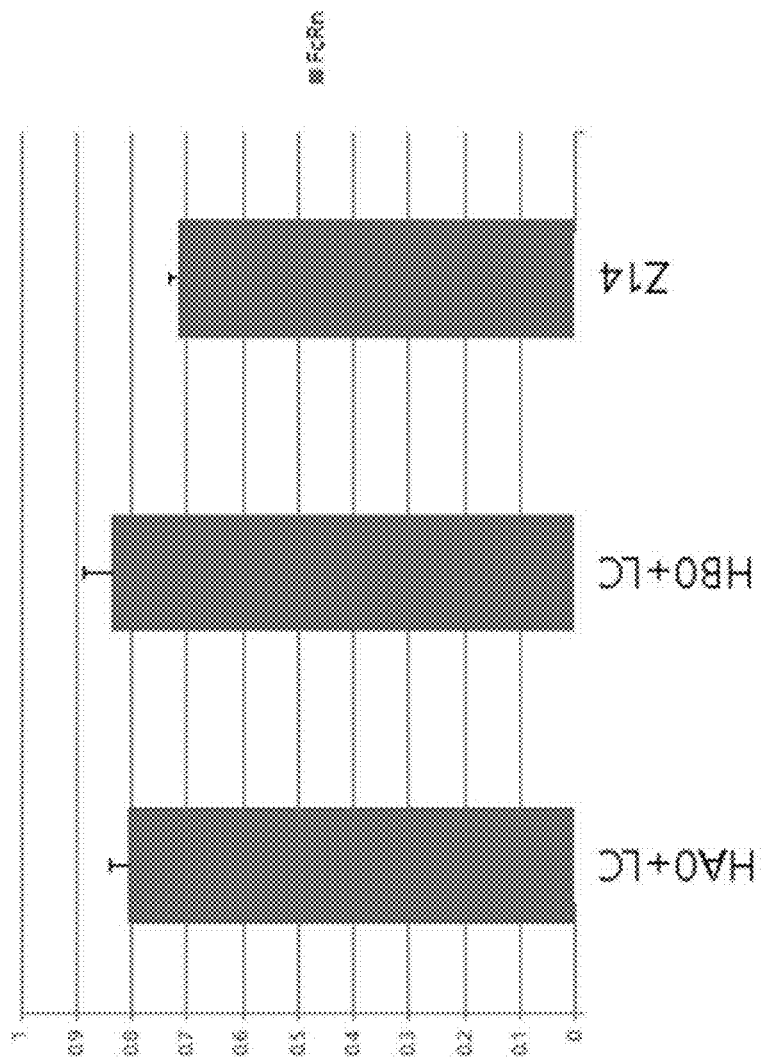
FIG. 17 shows that the Fc of antibodies generated in the present invention binds well with receptors.

Result analysis showed that the receptor binding activities of the Fc domains of 4D9 (HA0+LC), 2B9 (HB0+LC), and Z14 antibodies were not significantly different (FIG. 17).

EXAMPLE 5

Figure 18:
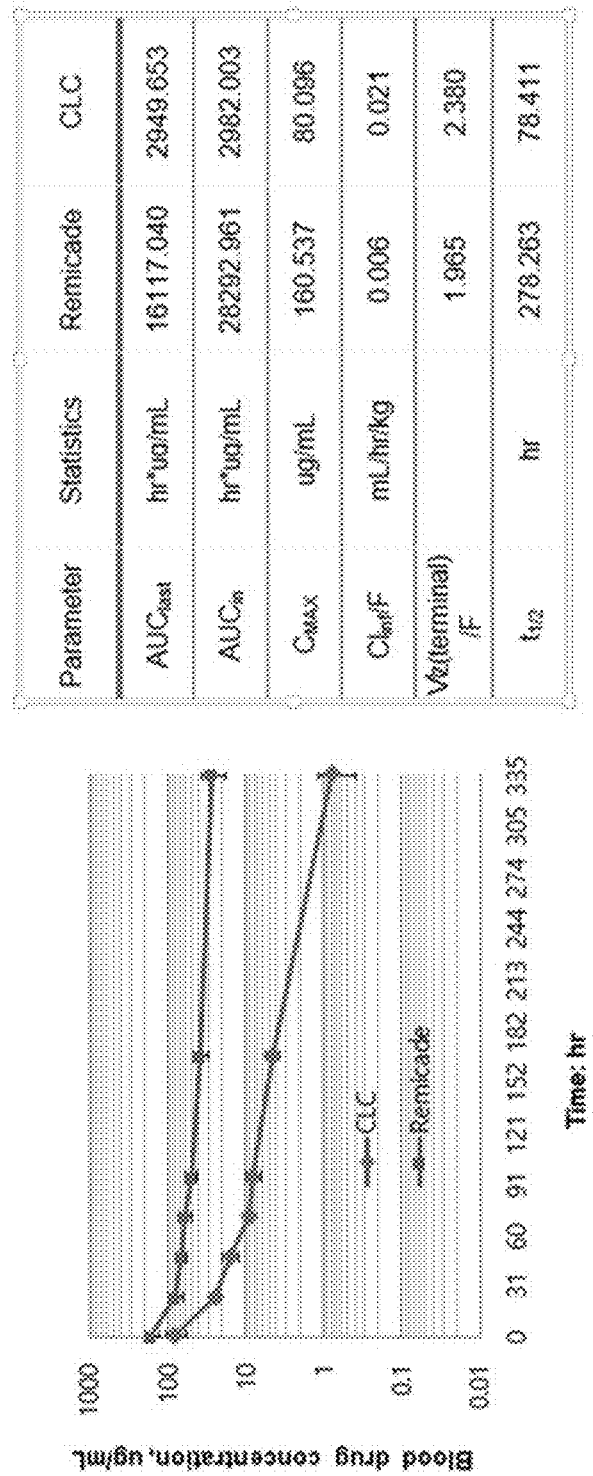
FIG. 18 shows pharmacokinetic data of BsAbs having the common light chain manufactured by the present invention.

Pharmacokinetic Analysis of Bispecific Antibodies Manufactured in the Present Invention 10 mg/ml of Remicade and 4 mg/kg of B6CBA were injected into mice CLC-BsAb, sample concentrations were measured up to 14 days after administration. There was no significant difference in the profile of the concentrations between the two antibodies. In order to analyze the pharmacokinetic parameters between Remicade and CLC-BsAbs, ANOVA test was performed with several pharmacokinetic parameters (CL, V1, AUC, MRT, t1/2), which was calculated by analysis of NCA and two-compartment model (see FIG. 18).

EXAMPLE 6

Correct Pairing of the Heavy Chains (HC) and the Light Chains (LC) of Antibodies Manufactured in the Present Invention To solve the problem at the step of pairing of HC/LC chains, 12 hydrophobic residues (Y36, A43, P44, Y87, Y96 and F98 of VL domain, and V37, F45, W47, W50, Y91, and W103 of the VH domain) and 9 hydrophobic (F116, F118, L133 and L135 within the CL domain, and L128, A141, L145, F170 and V185 of the CH1 domain) have been considered as preferred modification sites.

A. Analytical Method of HC/LC Pairing

Novel HC/LC pairing analysis was devised in order to facilitate the search for the correct modification sites leading correct HC/LC pairing.

If the modification of proteins allows 100% discrimination of chains, a light chain LP (a positively charged light chain) is combined with a heavy chain HN (a negatively charged heavy chain), but not with HP (a positively charged heavy chain), to form a homologous HN/LP antibodies consisting of the 50 kD HN and 25 kD CP (positively charged common light chains). It can be confirmed by the reduced SDS-PAGE gel. If the modification of proteins cannot distinguish the chains, the light chain LP will be combined with the heavy chains HP and HN, and will result in the formation of three different Abs. It will form 60 kD HP as well as 50 kD HN and 25 kD LP in the reduced SDS-PAGE gel.

B. Design for Symmetry and Asymmetry

Figure 19:
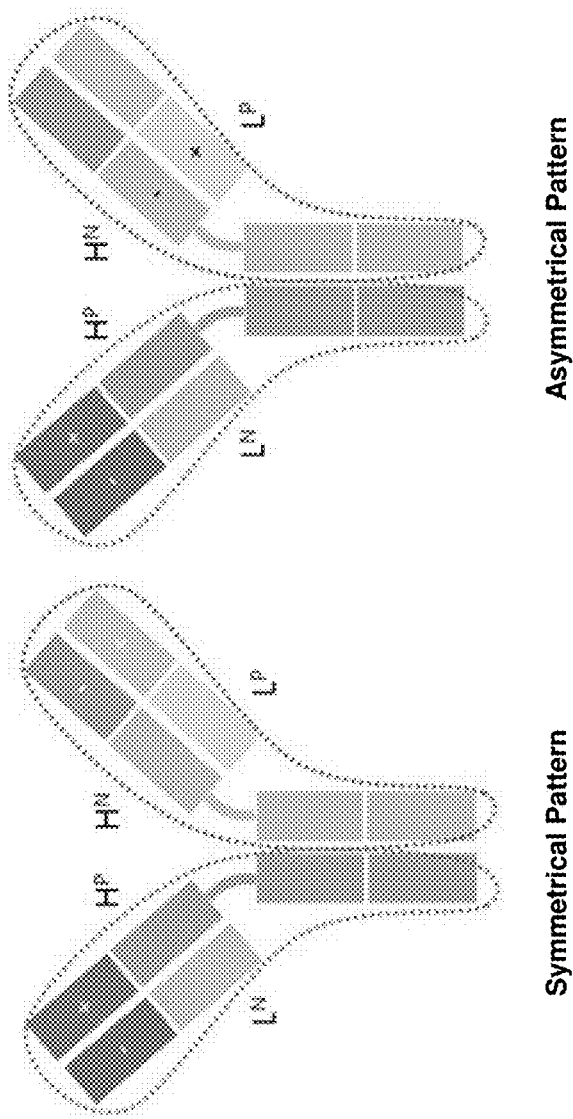
FIG. 19 is a schematic diagram showing that, in the manufacture of antibodies in accordance with the present invention, binding of the heavy and light chains is distinguished to be symmetrical or asymmetrical relative to the positions of the charge.

Modification ws made in two different designs. The pattern of charge distributions in the two Fab domains may be symmetrical or asymmetrical (see FIG. 19).

C. Variants pf HC/LC Pairing

Entire 21 hydrophobic residues were, separately or in combination, modified to lectrotatically interacting pair residues, and associated in 21 sets of the variants (see Table 7).

TABLE 7

| Design | Set Name | HP Name | HP (2B9) | HN Name | HN (4D9) | LP Name | LP | LN Name | LN |
|---|---|---|---|---|---|---|---|---|---|
| Symmetry | V1 | HPa | F45K | HNa | F45D | LPa | F98K | LNa | F98D |
| | V3 | HPc | W103K | HNc | W103D | LPc | P44K | LNc | P44D |
| | V4 | HPd | V37K | HNd | V37D | LPa | F98K | LNa | F98D |
| | V5 | HPa | F45K | HNa | F45D | LPe | Y87K | LNe | Y87D |
| | W1 | HP1 | L128K | HN1 | L128D | LP1 | F118K | LN1 | F118D |
| | W2 | HP2 | A141K | HN2 | A141D | LP2 | F116K | LN2 | F116D |
| | W3 | HP3 | L145K | HN3 | L145D | LP3 | V133K | LN3 | V133D |
| | W4 | HP4 | V185K | HN4 | V185D | LP4 | L135K | LN4 | L135D |
| | W5 | HP1 | L128K | HN1 | L128D | LP3 | V133K | LN3 | V133D |
| | W6 | HP2 | A141K | HN2 | A141D | LP4 | L135K | LN4 | L135D |
| | W7 | HP7 | L145K/ V185K | HN7 | L145D/ V185D | LP7 | V133K/ L135K | LN7 | V133D/ L135D |
| | W8 | HP8 | A141K/ V185K | HN8 | A141D/ V185D | LP8 | F116K/ L135K | LN8 | F116D/ L135D |
| Asymmetry | V3P | HPc | W103K | H0 | — | L0 | — | LNc | P44D |
| | W2P | HP2 | A141K | H0 | — | L0 | — | LN2 | F116D |
| | W4P | HP4 | V185K | H0 | — | L0 | — | LN4 | L135D |
| | V3W4 | HPc | W103K | HN4 | V185D | LP4 | L135K | LNc | P44D |
| | W4V3 | HP4 | V185K | HNc | W103D | LPc | P44K | LN4 | L135D |
| | V3V1 | HPc | W103K | HNa | F45D | LPa | F98K | LNc | P44D |
| | V3W1 | HPc | W103K | HN1 | L128D | LP1 | F118K | LNc | P44D |

The degree of correct HC/LC pairing in the variant sets was measured by the method of HC/LC pairing analysis, which was previously described.

SDS-PAGE Analysis

Figure 20:
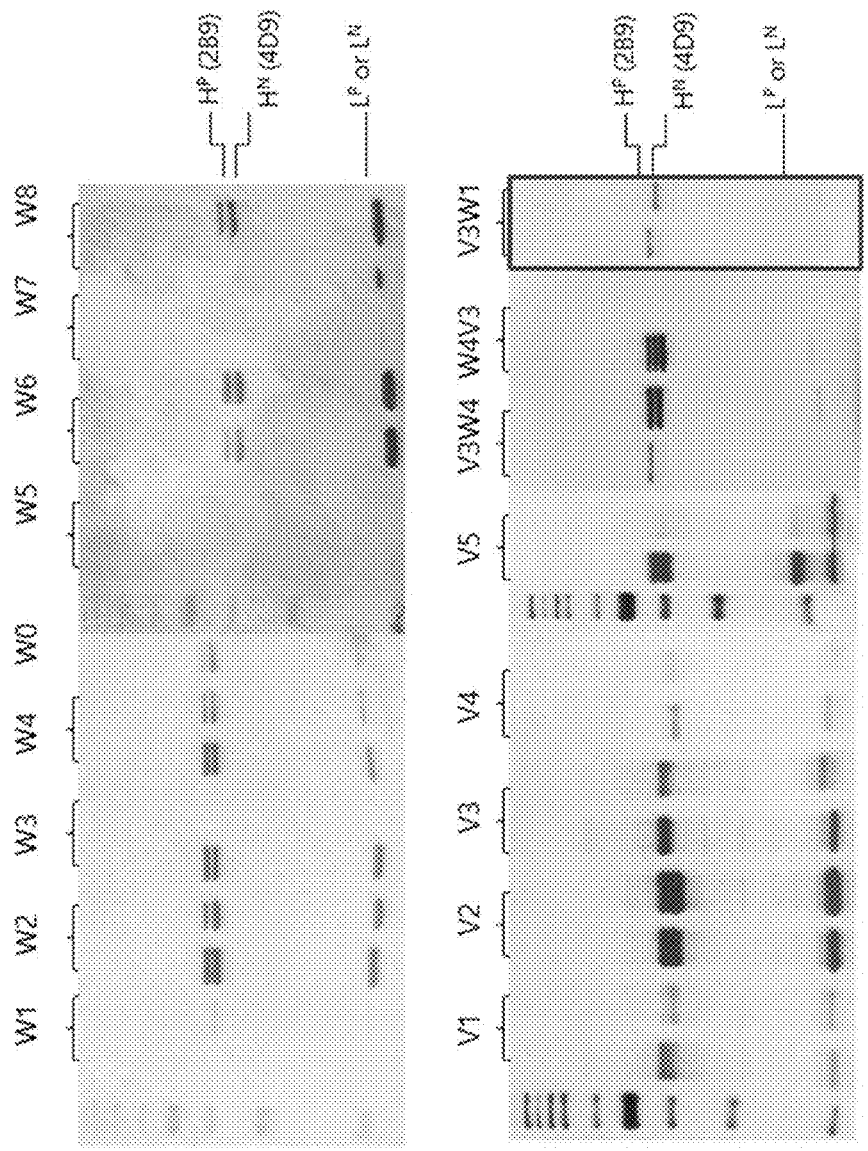
FIG. 20 shows that pairing of the heavy chains and the light chains of the antibodies in accordance with the present invention is correct. The combination of V3W1 in Table 7 is the most excellent pair between the heavy chain and the light chain.

V3W1 set was chosen as the best variant leading to modified to correct HC/LC pairing among 21 sets (see FIG. 20).

The invention claimed is:

1. A method of preparation of a protein with increased chain selectivity, the method comprising the following steps:
    (a) selecting at least two pairs of hydrophobic amino acids from the group consisting of 351 leucine and 351 leucine pair, 395 proline and 397 valine pair, and 395 proline and 395 proline pair between CH3 domains in a protein comprising two Fc domains of human IgG1 of SEQ ID NO: 1, or IgG4 of SEQ ID NO: 4;
    (b) modifying one hydrophobic amino acid to a positive charged amino acid selected from the group consisting of lysine, arginine and histidine, and the other hydrophobic amino acid to a negative charged amino acid selected from the group consisting of aspartic acid and glutamic acid, in the selected pairs of hydrophobic amino acids; and
    (c) binding with electrostatic interaction by contacting between the positive charged amino acid and the negative charged amino acid.

2. A protein comprising two Fc domains of human IgG1 of SEQ ID NO: 1, or IgG4 of SEQ ID NO: 4, characterized in that at least two hydrophobic amino acid pairs selected from the group consisting of 351 leucine and 351 leucine pair, 395 proline and 397 valine pair, and 395 proline and 395 proline pair between CH3 domains of the protein are mutated by substituting one hydrophobic amino acid of each amino acid pair with a positive charged amino acid selected from the group consisting of lysine, arginine and histidine, and the other hydrophobic amino acid with a negative charged amino acid selected from the group consisting of aspartic acid and glutamic acid, whereby electrostatic interaction is introduced between the mutated amino acids in the protein.

3. A protein comprising two Fc domains of human IgG1 of SEQ ID NO: 1, or IgG4 of SEQ ID NO: 4, wherein the protein comprises a mutation of Z4, Z6, Z7, Z8, Z10, Z11, Z12, or Z14 as defined in the following table:

|     | Chain A                  | Chain B                  |
| --- | ------------------------ | ------------------------ |
| Z4  | L351K/P395K              | L351D/P395D              |
| Z6  | T394K/P395K              | T394D/P395D              |
| Z7  | T394K/V397K              | T394D/V397D              |
| Z8  | P395K/V397K              | P395D/V397D              |
| Z10 | L351K/T394K/P395K        | L351D/T394D/P395D        |
| Z11 | L351K/T394K/V397K        | L351D/T394D/V397D        |
| Z12 | L351K/P395K/V397K        | L351D/P395D/V397D        |
| Z14 | L351K/T394K/P395K/V397K  | L351D/T394D/P395D/V397D  |

4. The protein according to claim 2 wherein the protein is a fusion antibody comprising a pair of ectodomains selected from the group consisting of TNFR2 (tumor necrosis factor receptor 2), Her3 (human epidermal growth factor receptor 3), Tie2 (angiopoietin receptor 2), TGFbR1 (transforming growth factor, beta receptor 1), BMPR1b (bone morphogenetic protein receptor type 1 b), Il-12R-b1 (interleukin 12 receptor subunit beta 1), IL-4Ra (interleukin 4 receptor alpha), ITGA4 (integrin subunit alpha 4), ITGA2B (integrin subunit alpha 2B), IFNAR1 (interferon-alpha receptor 1), IL-12A (interleukin 12 receptor subunit alpha), IL-4 (interleukin 4), IFN-alpha (interferon-alpha), BMP2 (bone morphogenetic protein 2), IL1 RL1 (interleukin 1 receptor-like 1), IL-17RA (interleukin 17 receptor alpha), IL-17A (interleukin 17 alpha), Fas (tumor necrosis factor receptor superfamily member 6), FltD2 (domain 2 of fms related tyrosine kinase), Her1 (human epidermal growth factor receptor 1), Tie1 angiopoietin receptor 1), TGFbR2 (transforming growth factor beta receptor 2), IL-12R-b2 (interleukin12 receptor subunit beta 2), IL-13Ra1 (interleukin 13 receptor subunit alpha 1), ITGB1 (integrin subunit beta 1), ITGB3 (integrin subunit beta 3), IFNAR2 (interferon-alpha/beta receptor 2), IL-12B (interleukin 12 beta), IL-13 (interleukin 13), IFN-beta (interferon beta), BMP7 (bone morphogenetic protein 7), IL-1RAP (Interleukin-1 receptor accessory protein), IL-17RC (interleukin 12 receptor C) and IL-17F (interleukin 17), and each of the selected pair of ectodomains is fused with each of the two Fc domains of the protein.

5. The protein according to claim 4 wherein the pair of ectodomains is Her3/FltD2 combination, Her1/Her3 combination, or Tie1/Tie2 combination.

6. The protein according to claim 2, wherein
    the protein is an antibody comprising two human IgG1- or IgG4-type heavy chains and two human kappa-type light chains, and further comprising a mutation selected from the group consisting of V1-V5, W1-W8, V2P, V3P, W4P, V3W4, W4V3, V3V1, and V3W1 as defined in the following table, thereby having an increased coupling between the heavy chain and the light chain:

|      | HP (heavy chain mutated with positive amino acid) | HN (heavy chain mutated with negative amino acid) | LP (light chain mutated with positive amino acid) | LN (light chain mutated with negative amino acid) |
| ---- | ------------- | ------------- | ------------- | ------------- |
| V1   | F45K          | F45D          | F98K          | F98D          |
| V3   | W103K         | W103D         | P44K          | P44D          |
| V4   | V37K          | V37D          | F98K          | F98D          |
| V5   | F45K          | F45D          | Y87K          | Y87D          |
| W1   | L128K         | L128D         | F118K         | F118D         |
| W2   | A141K         | A141D         | F116K         | F116D         |
| W3   | L145K         | L145D         | V133K         | V133D         |
| W4   | V185K         | V185D         | L135K         | L135D         |
| W5   | L128K         | L128D         | V133K         | V133D         |
| W6   | A141K         | A141D         | L135K         | L135D         |
| W7   | L145K/V185K   | L145D/V185D   | V133K/L135K   | V133D/L135D   |
| W8   | A141K/V185K   | A141D/V185D   | F116K/L135K   | F116D/L135D   |
| V3P  | W103K         | —             | —             | P44D          |
| W2P  | A141K         | —             | —             | F116D         |
| W4P  | V185K         | —             | —             | L135D         |
| V3W4 | W103K         | V185D         | L135K         | P44D          |
| W4V3 | V185K         | W103D         | P44K          | L135D         |
| V3V1 | W103K         | F45D          | F98K          | P44D          |
| V3W1 | W103K         | L128D         | F118K         | P44D.         |

7. The protein according to claim 6, wherein the mutation is V3W1.

8. The protein according to claim 2, wherein, the protein is an antibody comprising two human IgG1- or IgG4-type heavy chains and two human kappa-type light chains, and one or more hydrophobic amino acid pairs selected from the group consisting of 128 leucine and 118 phenylalanine pair, 128 leucine and 133 valine pair, 141 alanine and 116 phenylalanine pair, 141 alanine and 135 leucine pair, 145 leucine and 133 valine pair, 170 phenylalanine and 135 leucine pair, 185 valine and 118 phenylalanine pair, and 185 valine and 135 leucine pair between a CH1 domain of the heavy chain and a CL domain of the light chain are mutated by substituting one hydrophobic amino acid of each amino acid pair with a positive charged amino acid selected from the group consisting of lysine, arginine and histidine, and the other hydrophobic amino acid with a negative charged amino acid selected from the group consisting of aspartic acid and glutamic acid, thereby having an increased coupling between the heavy chain and the light chain.

9. The protein according to claim 3, wherein, the protein is an antibody comprising two human IgG1- or IgG4-type heavy chains and two human kappa-type light chains, and one or more hydrophobic amino acid pairs selected from the group consisting of 128 leucine and 118 phenylalanine pair, 128 leucine and 133 valine pair, 141 alanine and 116 phenylalanine pair, 141 alanine and 135 leucine pair, 145 leucine and 133 valine pair, 170 phenylalanine and 135 leucine pair, 185 valine and 118 phenylalanine pair, and 185 valine and 135 leucine pair between a CH1 domain of the heavy chain and a CL domain of the light chain are mutated by substituting one hydrophobic amino acid of each amino acid pair with a positive charged amino acid selected from the group consisting of lysine, arginine and histidine, and the other hydrophobic amino acid with a negative charged amino acid selected from the group consisting of aspartic acid and glutamic acid, thereby having an increased coupling between the heavy chain and the light chain.

* * * * *